US009611357B2

(12) United States Patent
Avila et al.

(10) Patent No.: US 9,611,357 B2
(45) Date of Patent: *Apr. 4, 2017

(54) CHEMICALLY MODIFIED DENDRIMERS

(71) Applicant: Genzyme Corporation, Cambridge, MA (US)

(72) Inventors: Luis Z. Avila, Arlington, MA (US); Robert J. Miller, East Bridgewater, MA (US); Lauren Elizabeth Young, Hampton, NH (US); Rajesh Vasant Kamath, Shrewsbury, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/966,935

(22) Filed: Dec. 11, 2015

(65) Prior Publication Data

US 2016/0096926 A1  Apr. 7, 2016

Related U.S. Application Data

(63) Continuation of application No. 14/151,165, filed on Jan. 9, 2014, now Pat. No. 9,283,247, which is a continuation of application No. 12/142,266, filed on Jun. 19, 2008, now Pat. No. 8,658,148.

(60) Provisional application No. 60/945,815, filed on Jun. 22, 2007.

(51) Int. Cl.
*C08G 69/48* (2006.01)
*C08G 69/08* (2006.01)
*C08G 73/02* (2006.01)
*C08G 83/00* (2006.01)
*A61K 31/785* (2006.01)

(52) U.S. Cl.
CPC ............ *C08G 69/48* (2013.01); *A61K 31/785* (2013.01); *C08G 69/08* (2013.01); *C08G 73/028* (2013.01); *C08G 83/003* (2013.01)

(58) Field of Classification Search
CPC .. A61K 38/00; A61K 31/785; A61K 39/3955; A61K 39/39558; A61K 47/48215; A61K 51/1027; A61K 47/48246; A61K 9/0019; A61K 9/113; A61K 9/1647; A61K 9/2027; A61K 9/2031; A61K 9/4866; C07K 2317/77; C08G 83/003; C08G 69/48; C08G 69/08
USPC ............ 424/78.08, 78.27, 78.29, 450, 78.17; 435/68.1; 528/329.1, 310, 424, 422, 425, 528/373, 35; 977/754; 526/351
See application file for complete search history.

(56) References Cited

U.S. PATENT DOCUMENTS

| | | | |
|---|---|---|---|
| 4,289,872 A | 9/1981 | Denkewalter et al. |
| 4,410,688 A | 10/1983 | Denkewalter et al. |
| 4,507,466 A | 3/1985 | Tomalia et al. |
| 4,558,120 A | 12/1985 | Tomalia et al. |
| 4,568,737 A | 2/1986 | Tomalia et al. |
| 4,582,865 A | 4/1986 | Balazs et al. |
| 4,587,329 A | 5/1986 | Tomalia et al. |
| 4,713,448 A | 12/1987 | Balazs et al. |
| 5,017,229 A | 5/1991 | Burns et al. |
| 5,099,013 A | 3/1992 | Balazs et al. |
| 5,153,724 A | 10/1992 | Miyoshi et al. |
| 5,356,883 A | 10/1994 | Kuo et al. |
| 5,527,524 A | 6/1996 | Tomalia et al. |
| 5,827,937 A | 10/1998 | Agerup |
| 6,022,524 A | 2/2000 | Maisano et al. |
| 6,426,067 B1 | 7/2002 | Matthews et al. |
| 6,521,223 B1 | 2/2003 | Calias et al. |
| 6,548,081 B2 | 4/2003 | Sadazai et al. |
| 6,627,744 B2 | 9/2003 | Davis et al. |
| 6,921,819 B2 | 7/2005 | Piron et al. |
| 7,226,972 B2 | 6/2007 | Zhao et al. |
| 2002/0048598 A1* | 4/2002 | Malik ...................... B82Y 5/00 424/450 |
| 2002/0082362 A1 | 6/2002 | Brocchini et al. |
| 2002/0155523 A1* | 10/2002 | Sparks ................. G01N 33/533 435/68.1 |
| 2003/0180250 A1 | 9/2003 | Chauhan et al. |
| 2003/0215390 A1 | 11/2003 | Rosen |
| 2003/0224522 A1 | 12/2003 | De Jong et al. |
| 2004/0076680 A1 | 4/2004 | Soltes et al. |
| 2004/0097720 A1 | 5/2004 | Bott et al. |
| 2004/0180852 A1 | 9/2004 | Schengrund et al. |
| 2004/0228831 A1 | 11/2004 | Belinka, Jr. et al. |
| 2005/0090553 A1 | 4/2005 | Shapiro |
| 2005/0136122 A1 | 6/2005 | Sadozai et al. |

FOREIGN PATENT DOCUMENTS

| | | |
|---|---|---|
| DE | 19703718 | 7/1997 |
| EP | 416250 | 3/1991 |
| EP | 607222 | 7/1994 |
| EP | 882454 | 12/1998 |
| EP | 1171136 | 1/2002 |
| FR | 2734268 | 11/1996 |

(Continued)

OTHER PUBLICATIONS

Arbuzov et al, "Synthesis, anti-inflammatory and analgesic activities of N-acylureas" Khimiko-Farmatsevticheskii Zhurnal, 23(6):682-3, (1989).
Heindel et al., "Carboxymethyldextran Lactone: A Preactivated Polymer for Amine Conjugations" Bioconjugate Chemistry 5:98-100, 1994.
Jayaraman et al., "Synthesis of Carbohydrate-Containing Dendrimers. 5. Preparation of Dendrimers Using Unprotected Carbohydrates" Tetrahedron Letters 38(38):6767-6770, 1997.
Kuo et al., "Chemical Modification of Hyaluronic Acid by Carbodiimides" Bioconjugate Chemistry 2(4):232-241, 1991.
Kutschy et al., "New Synthesis of N-Acylurea Derivatives" Collection of Czechoslovak Chemical Communications, 58(3): 575-587, 1993.
Lee et al., "Biochemical and Immunological Properties of Cytokines Conjugated to Dendritic Polymers" Biomedical Microdevices, 6(3):191-202, 2004.

(Continued)

*Primary Examiner* — Gregory Listvoyb
(74) *Attorney, Agent, or Firm* — Fish & Richardson P.C.

(57) ABSTRACT

Dendrimers comprising N-acyl urea terminal moieties are described herein. The dendrimers can be used, for example, in the treatment of arthritis.

19 Claims, 26 Drawing Sheets

(56) References Cited

FOREIGN PATENT DOCUMENTS

| | | |
|---|---|---|
| JP | 2002265495 | 9/2002 |
| WO | WO 88/01178 | 2/1988 |
| WO | WO 88/01179 | 2/1988 |
| WO | WO 88/01180 | 2/1988 |
| WO | WO 93/06868 | 4/1993 |
| WO | WO 94/02517 | 2/1994 |
| WO | WO 95/24221 | 9/1995 |
| WO | WO 98/03573 | 1/1998 |
| WO | WO 00/59490 | 10/2000 |
| WO | WO 01/41640 | 6/2001 |
| WO | WO 01/66601 | 9/2001 |
| WO | WO 02/09792 | 2/2002 |
| WO | WO 03/080121 | 10/2003 |
| WO | WO 03/089010 | 10/2003 |
| WO | WO 03/093469 | 11/2003 |
| WO | WO 2004/009665 | 1/2004 |
| WO | WO 2004/009666 | 1/2004 |
| WO | WO 2004/041310 | 5/2004 |
| WO | WO 2005/007197 | 1/2005 |
| WO | WO 2005/054279 | 6/2005 |
| WO | WO 2005/066215 | 7/2005 |

OTHER PUBLICATIONS

Lei et al., "Quantification of Residual EDU (n-ehtyl-N'-(dimethylaminopropyl) carbodiimide (EDC) hydrolyzed urea derivative) and other residual by LC-MS/MS" Journal of Chromatography, B, 813:103-112, 2004.

Ruiz-Perez et al., "Protection against Lethal Intra-abdominal Sepsis by 1-(3dimethylaminopropyl)-3-ethylurea" Journal of Infectious Diseases, 188:378-387, 2003.

Shaunak et al., "Polyvalent dendrimer glucosamine conjugates prevent scar tissue formation" Nature Biotechnology, 22(8):977-984, 2004.

Soltes et al., "Associating Hyaluronan Derivatives: A Novel Horizon in Viscosupplementation of Osteoarthritic Joints" Chemistry & Biodiversity, 1(3):468-472, 2004.

Soltes et al., "Molecular Characterization of two host-guest associating hyaluronan derivatives" Biomedical Chromatography, 17(6): 376-384, 2003.

Young et al., "Preparation of cross-linked hyaluronic acid film using 2-chloro-l-methylpyridinium iodide or water-soluble 1-ethyl-(3,3-dimethylaminopropyl)carbodiimide" Journal of Biomaterials Science, Polymer Edition, 15(6):767-780, 2004.

\* cited by examiner

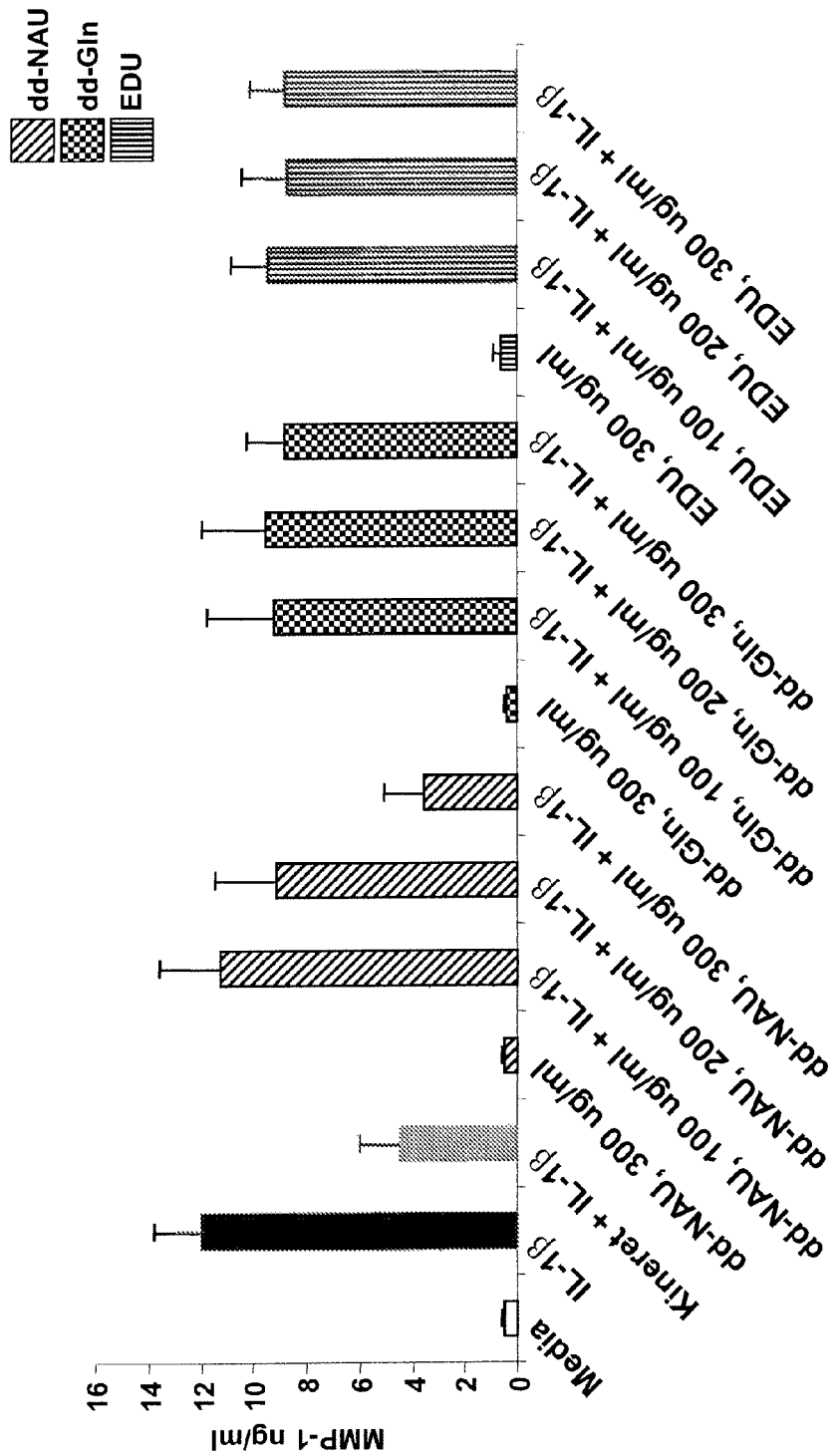
Figure 1: Effect of dd-NAU and dd-Gln on Levels of Active MMP-1 in Chondrocytes Stimulated with IL-1β

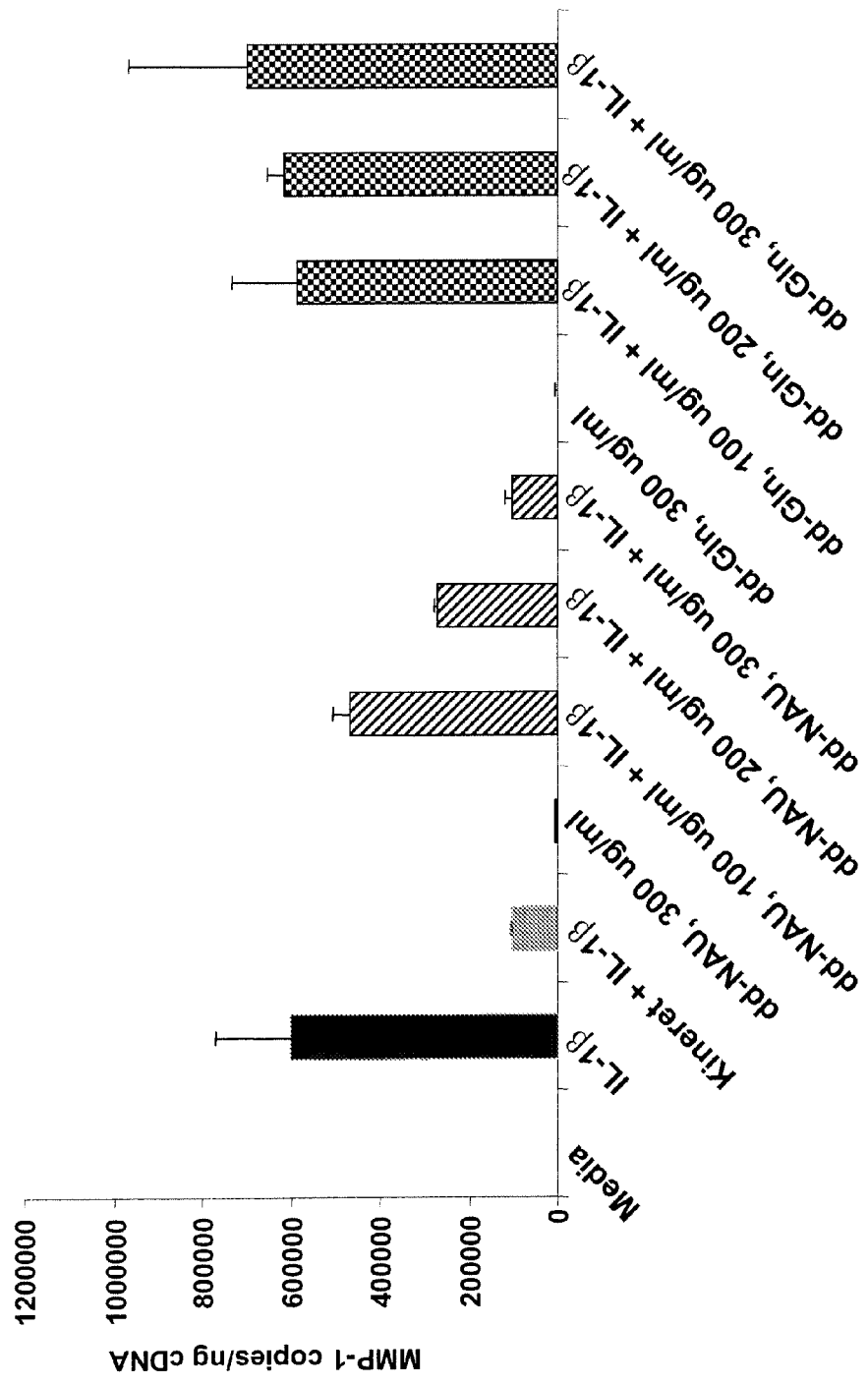

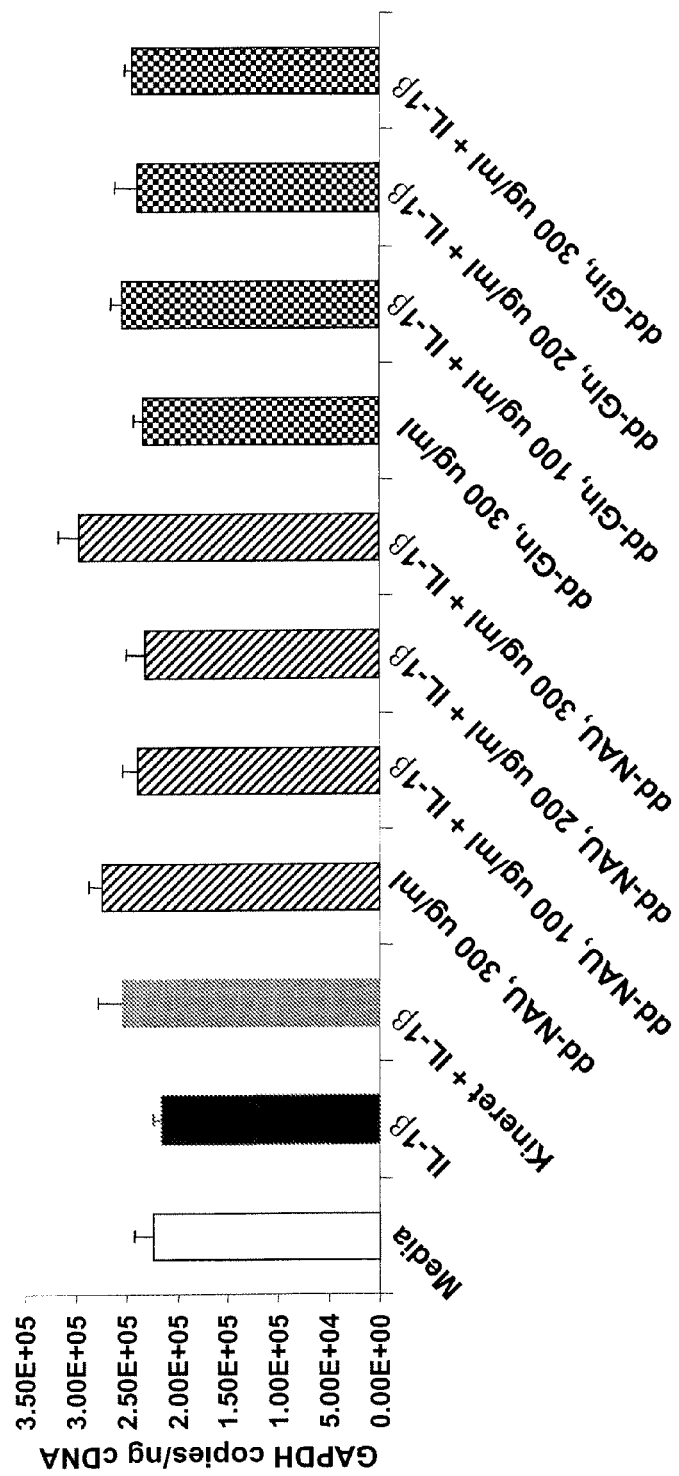
Figure 3: Real-time Quantitative PCR Analysis of GAPDH RNA from Cells Treated with dd-NAU and dd-Gln

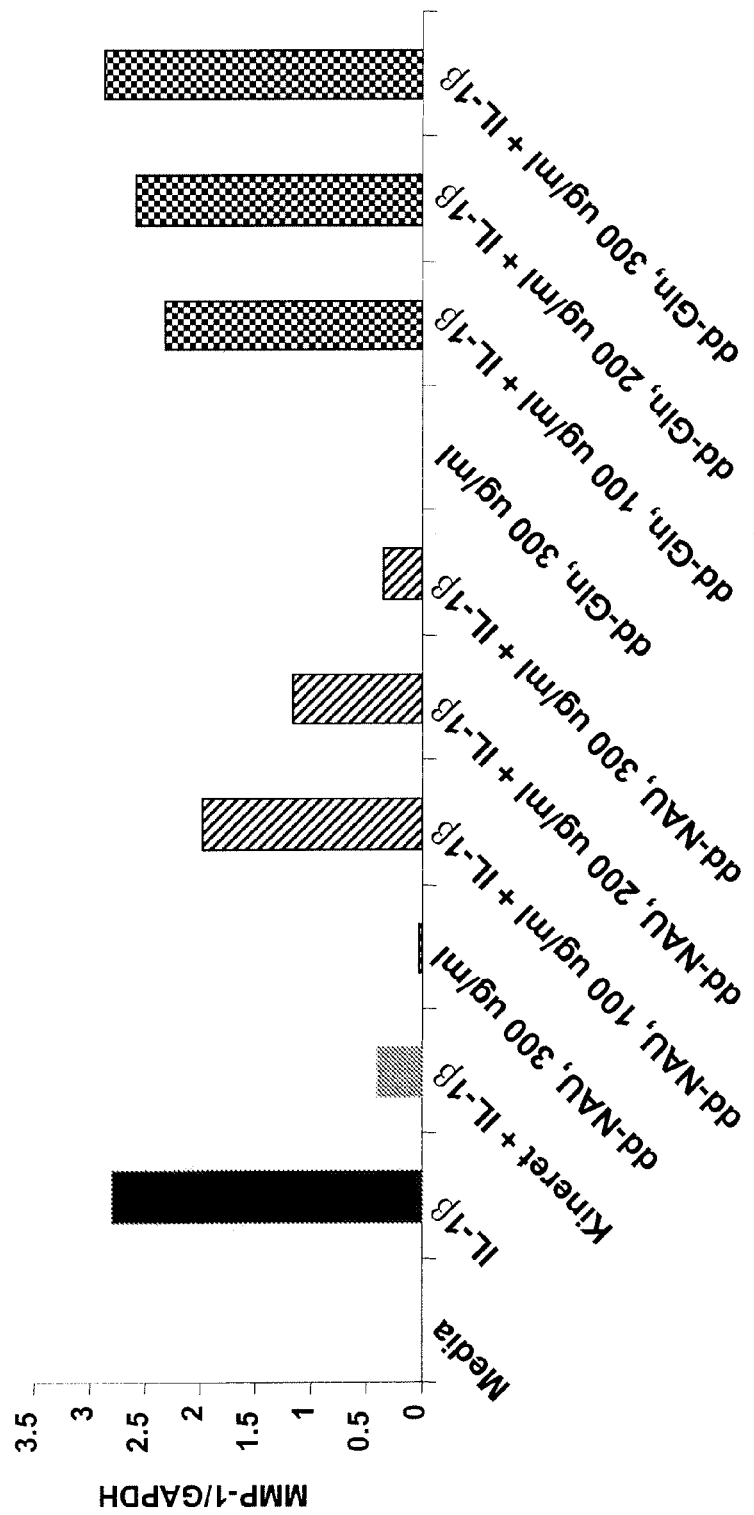
Figure 4: Real-time Quantitative PCR Analysis of MMP-1 Normalized to GAPDH

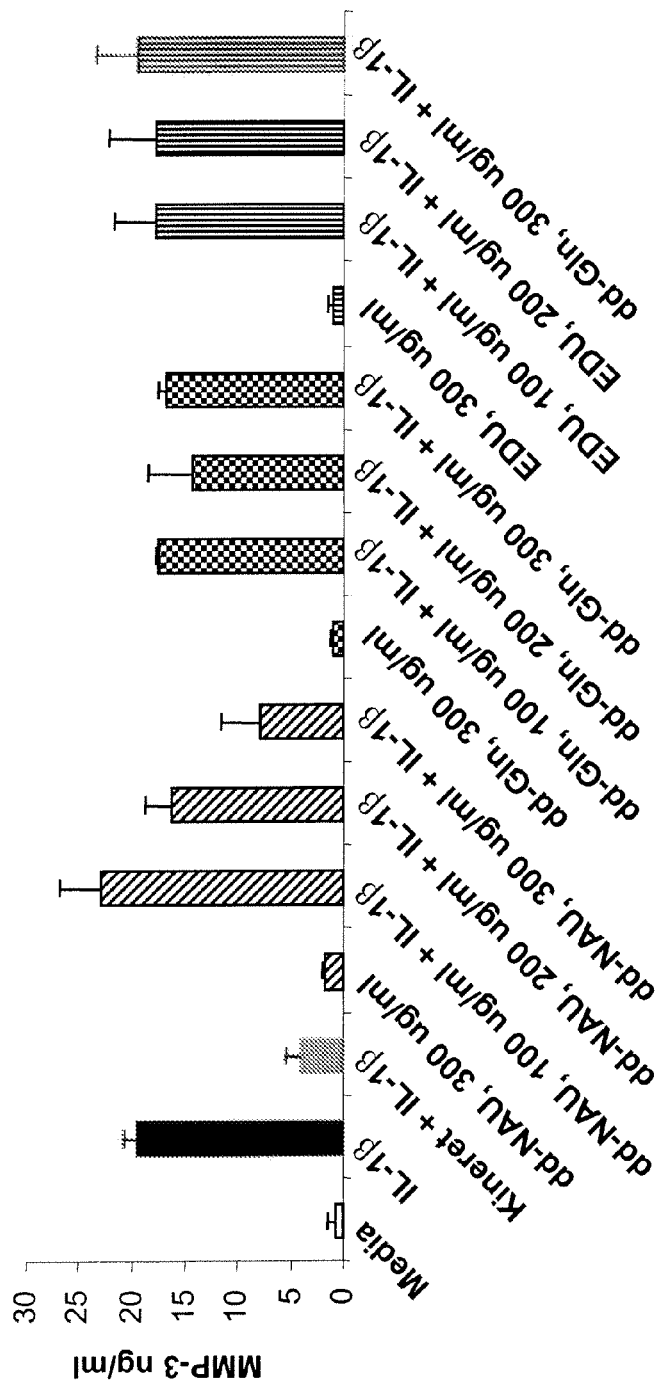
Figure 5: Effect of dd-NAU and dd-Gln on Levels of Active MMP-3 in Chondrocytes Stimulated with IL-1β

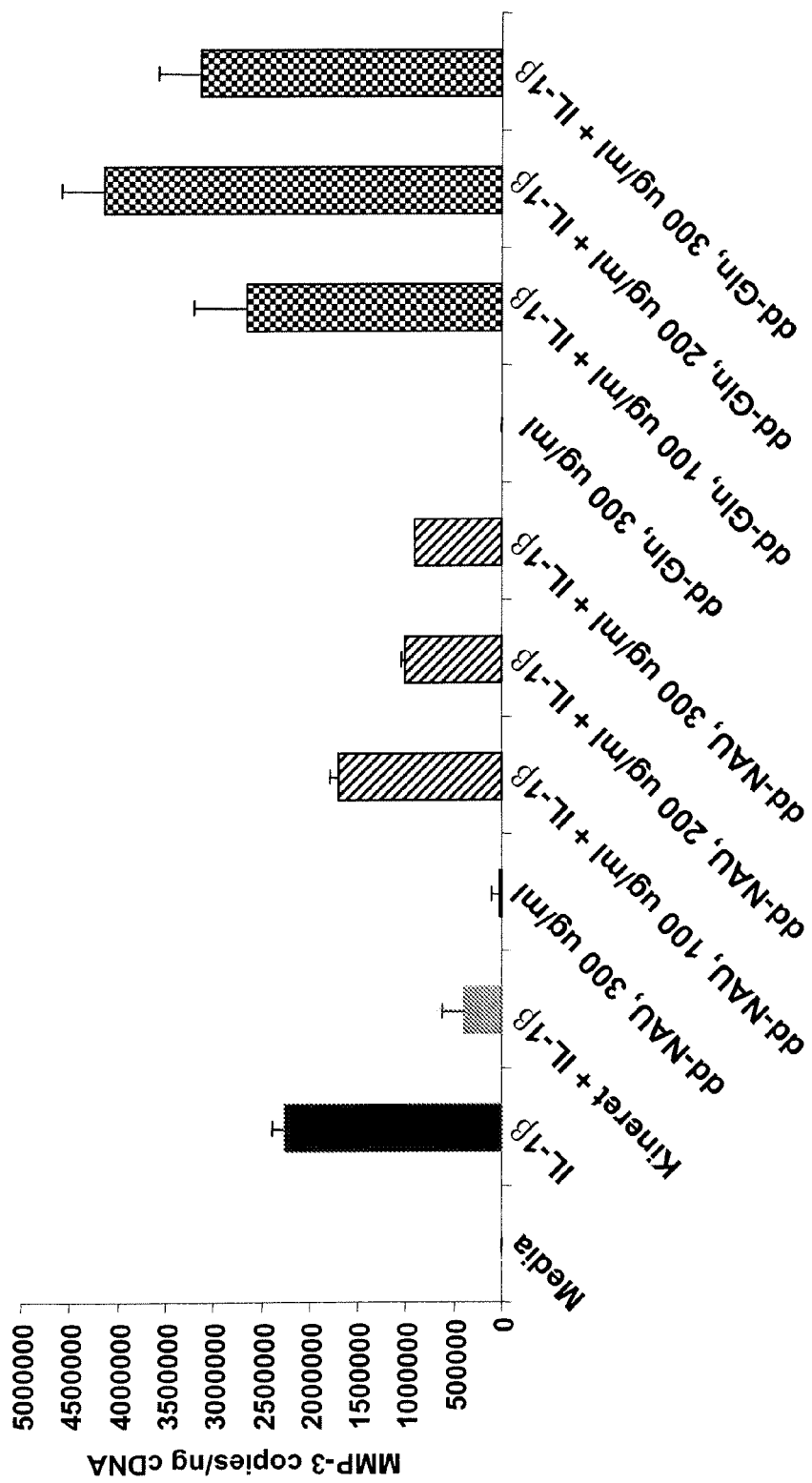
Figure 6: Real-time Quantitative PCR Analysis of MMP-3 RNA from Cells Treated with dd-NAU and dd-Gln

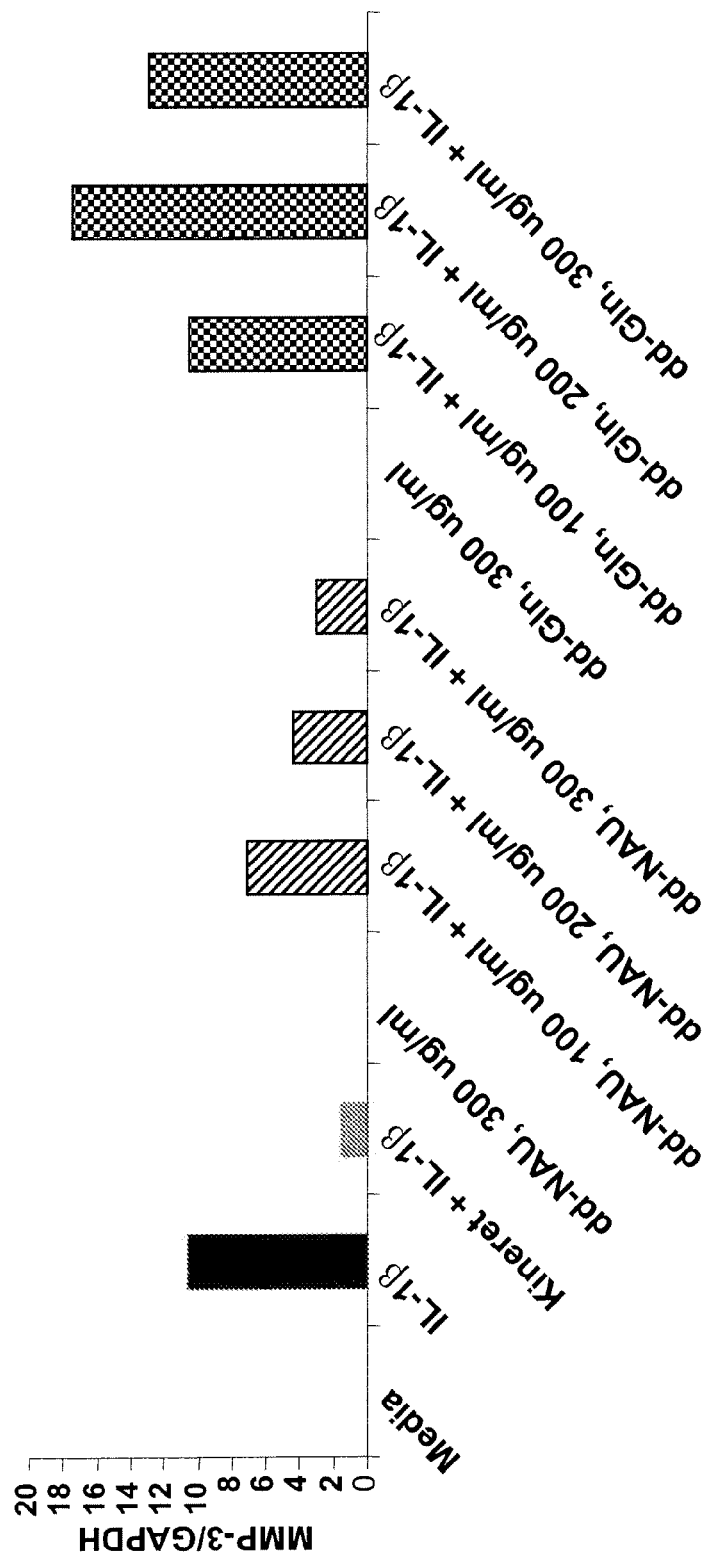

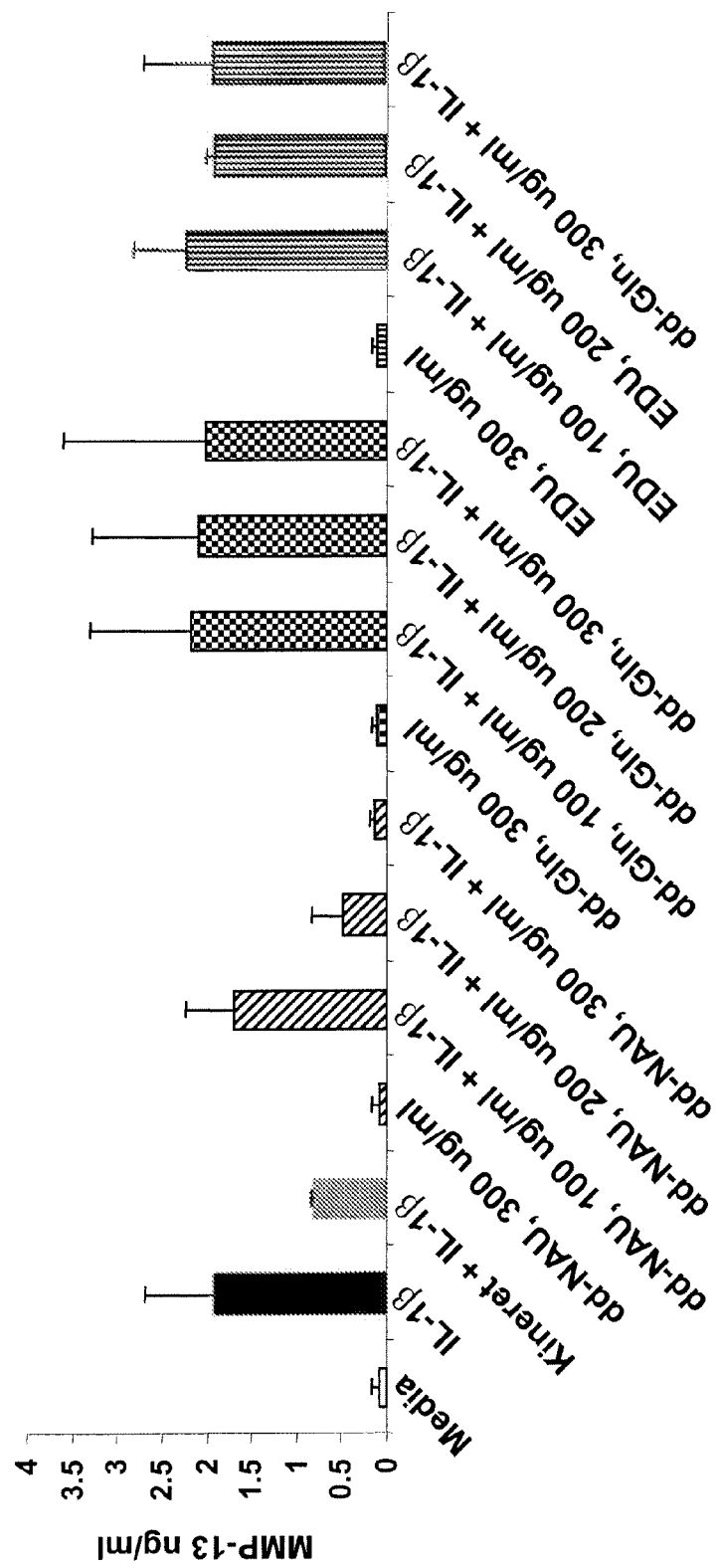
Figure 8: Effects of dd-NAU and dd-Gln on Levels of Active MMP-13 in Chondrocytes Stimulated with IL-1β

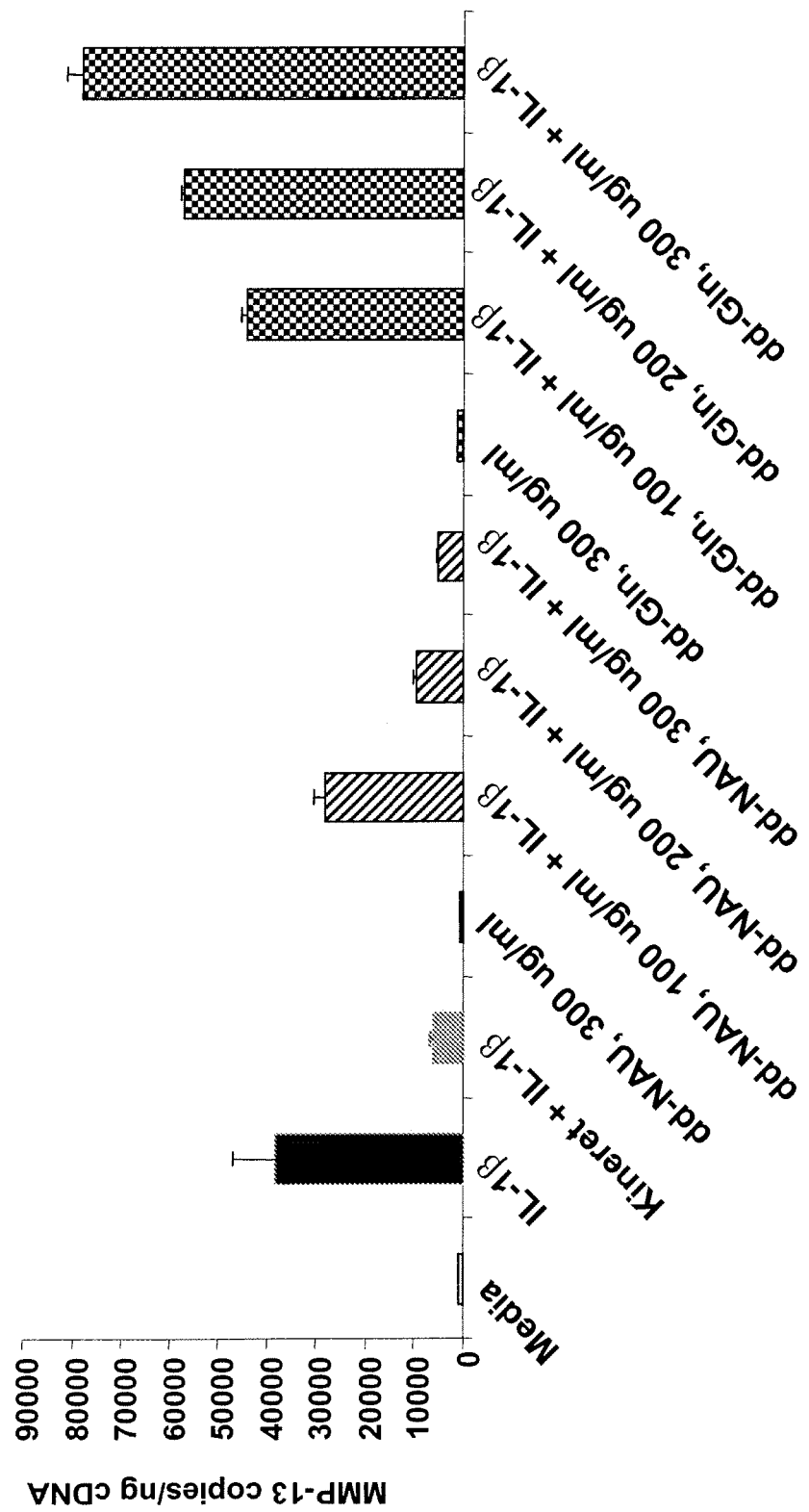
Figure 9: Real-time Quantitative PCR Analysis of MMP-3 RNA from Cells Treated with dd-NAU and dd-Gln

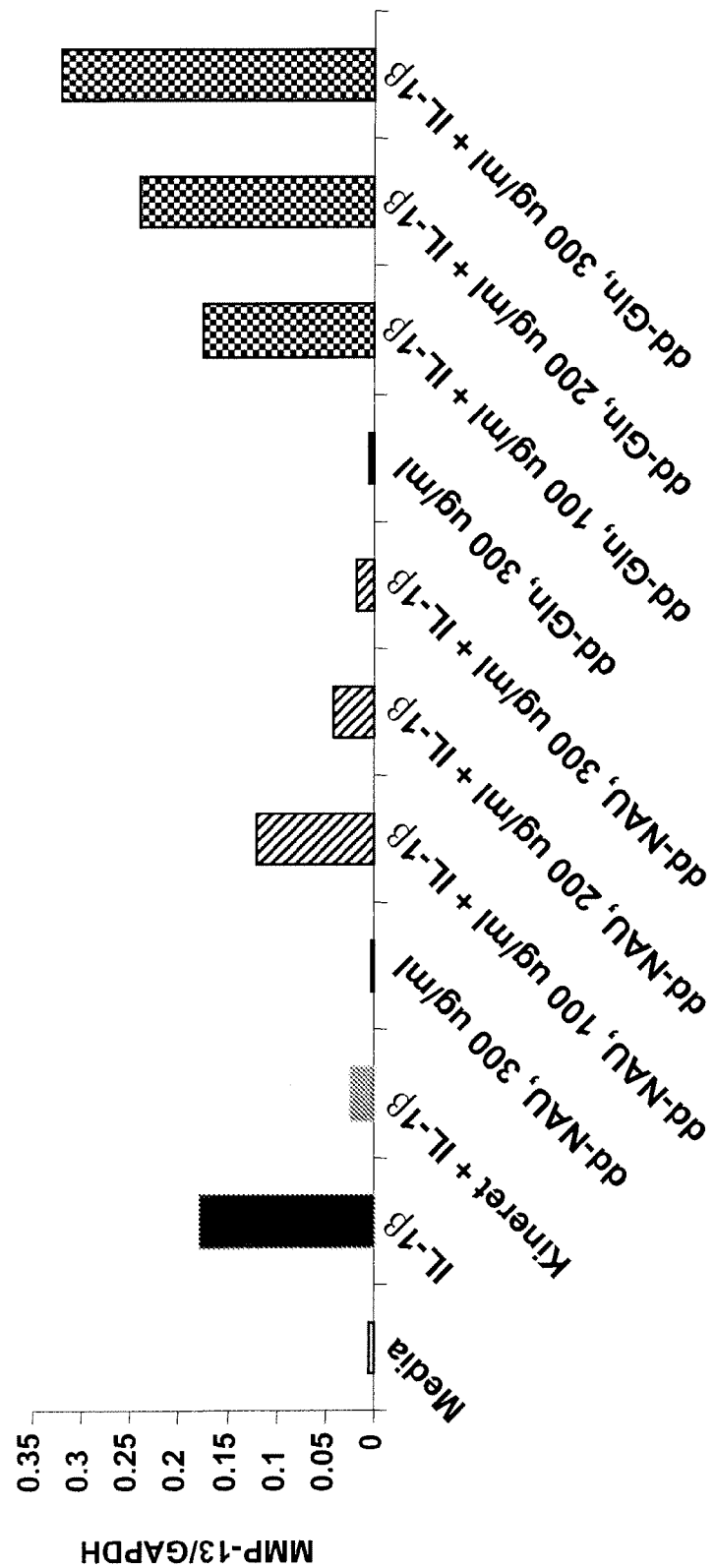

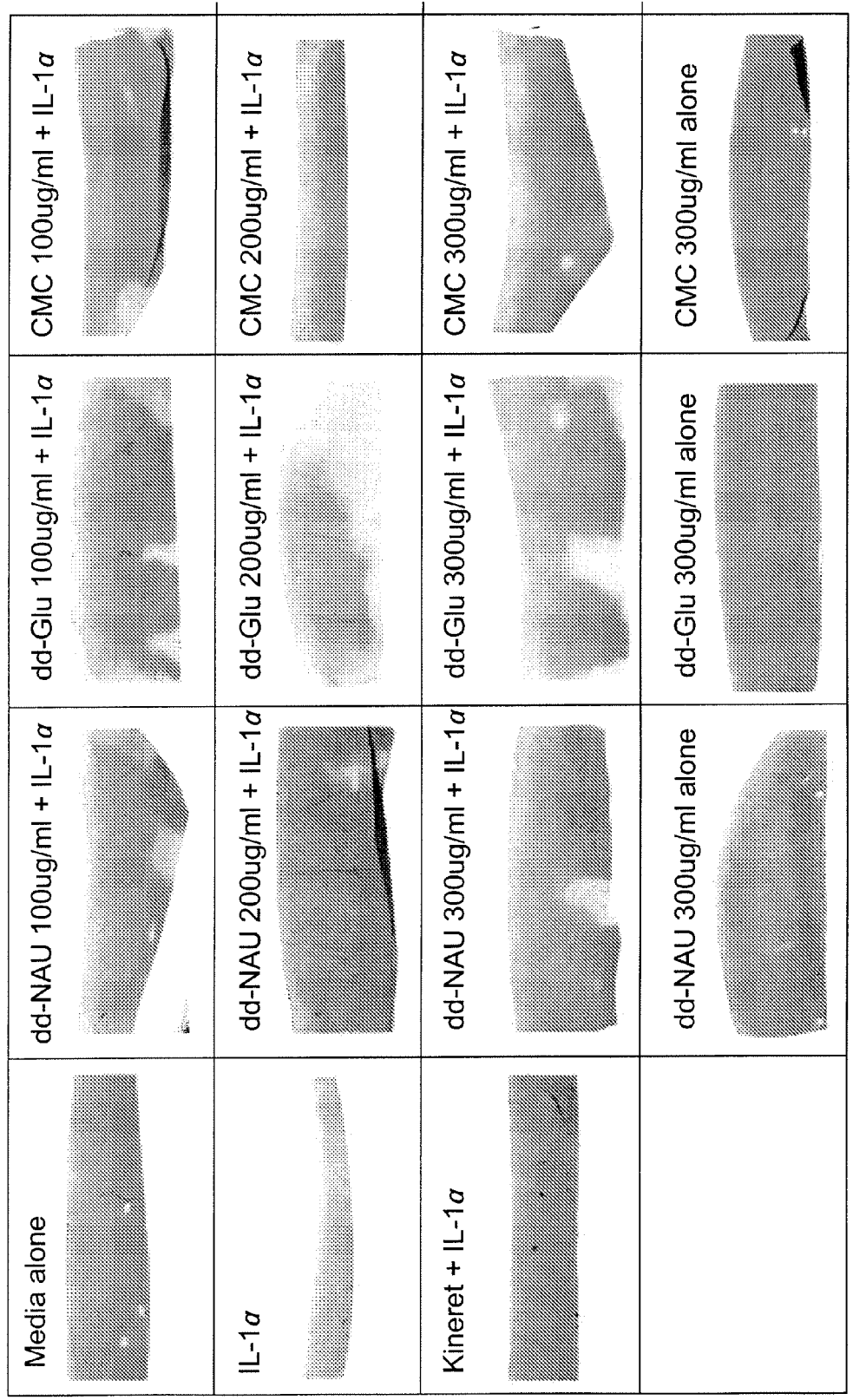
Figure 11: Histological Analysis of Bovine Cartilage explants

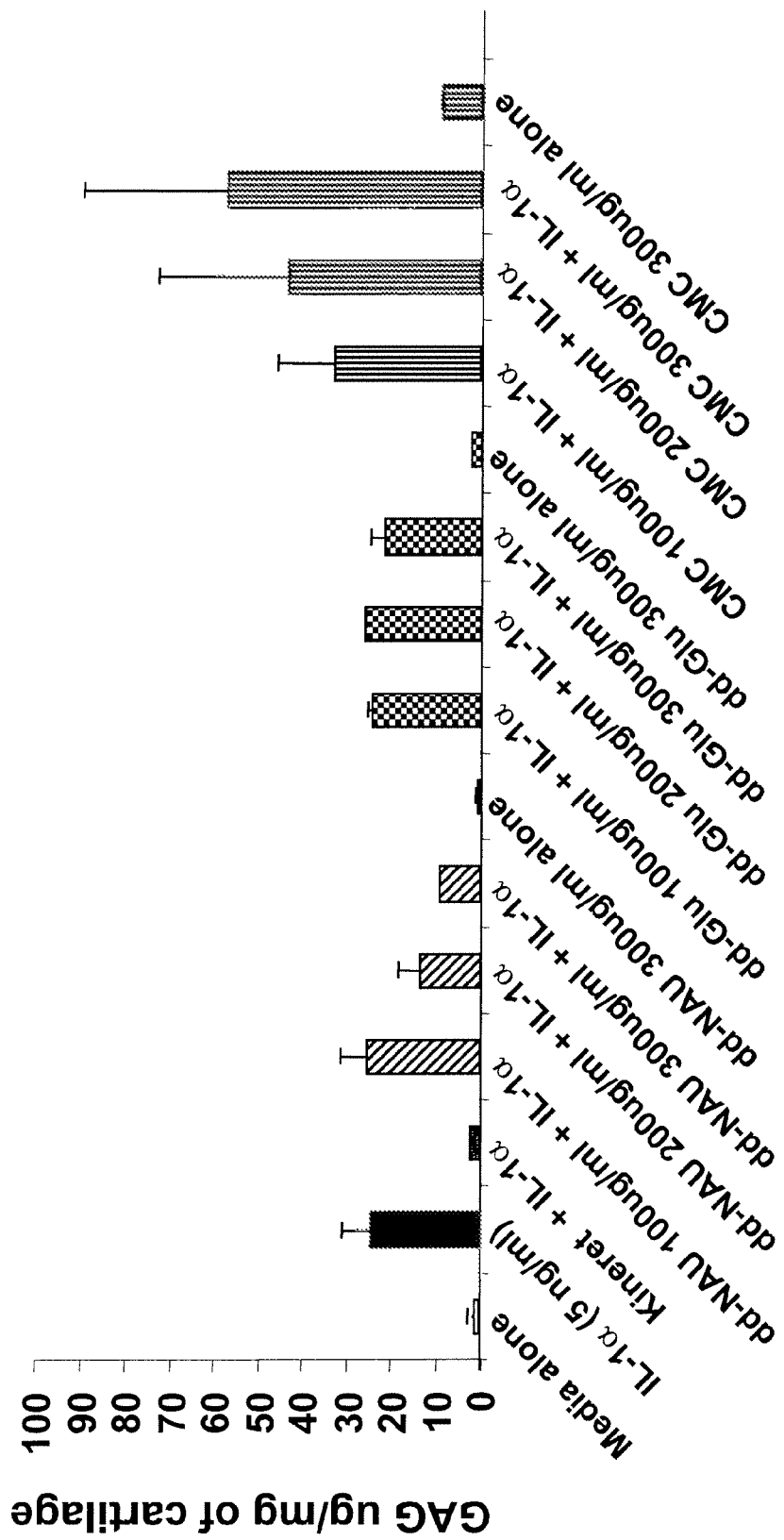
*Figure 12:* Chondroprotective Role of dd-NAU (Normalized to Wet Weight)

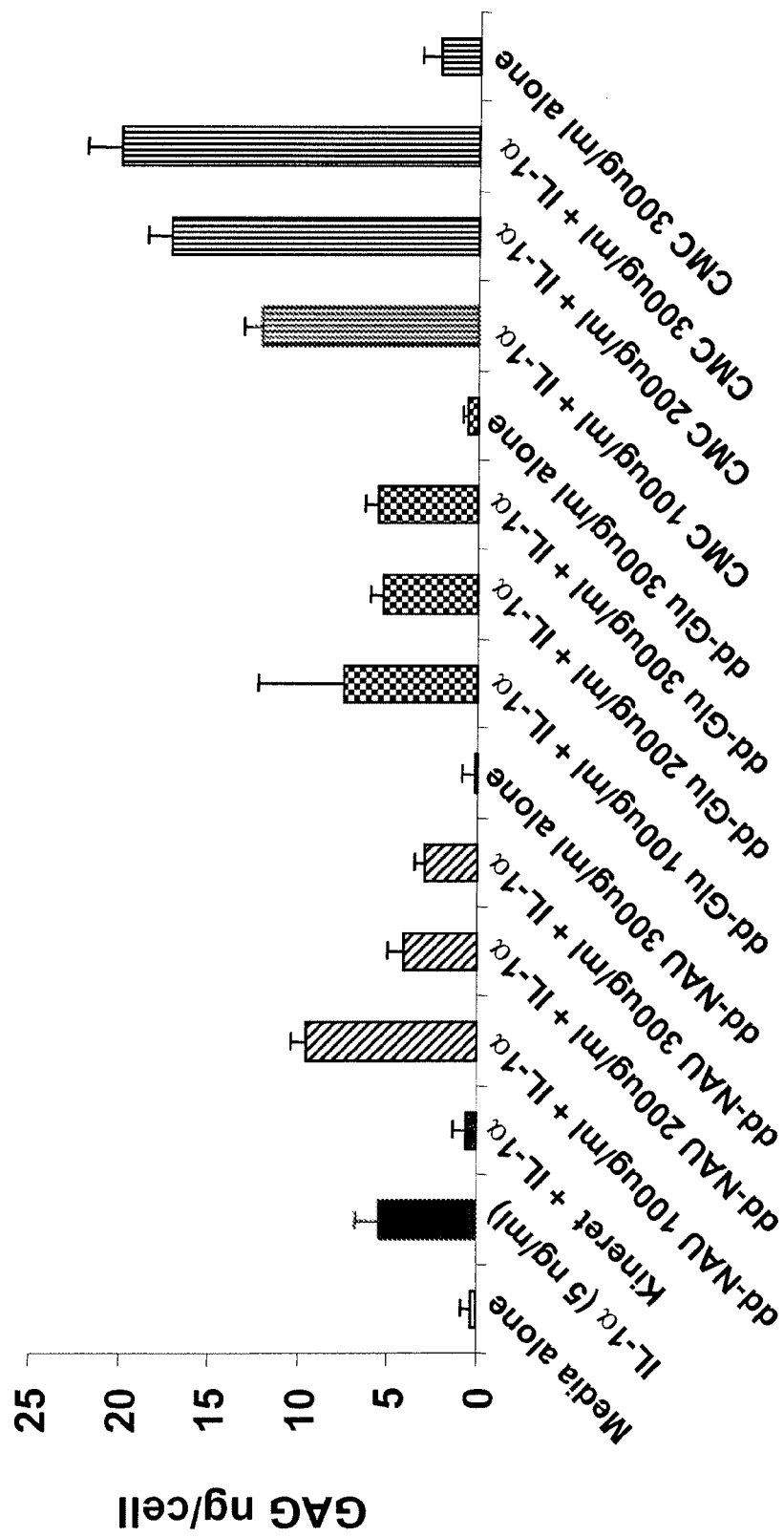
Figure 13: Chondroprotective Role of dd-NAU (Normalized to DNA)

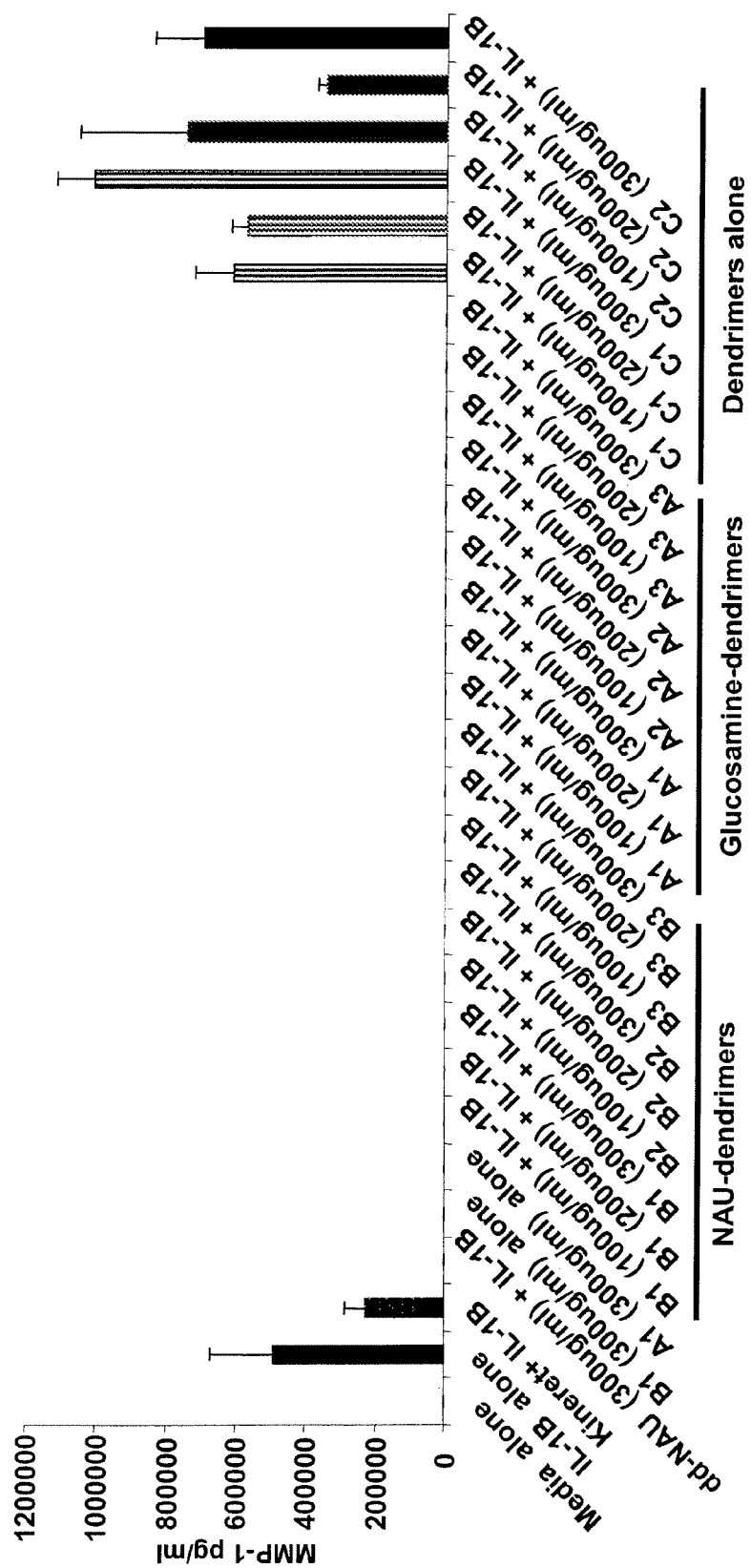
Figure 14: Effect of NAU- and Glucosamine dendrimers on MMP-1 production by human chondrocytes stimulated with IL-1β

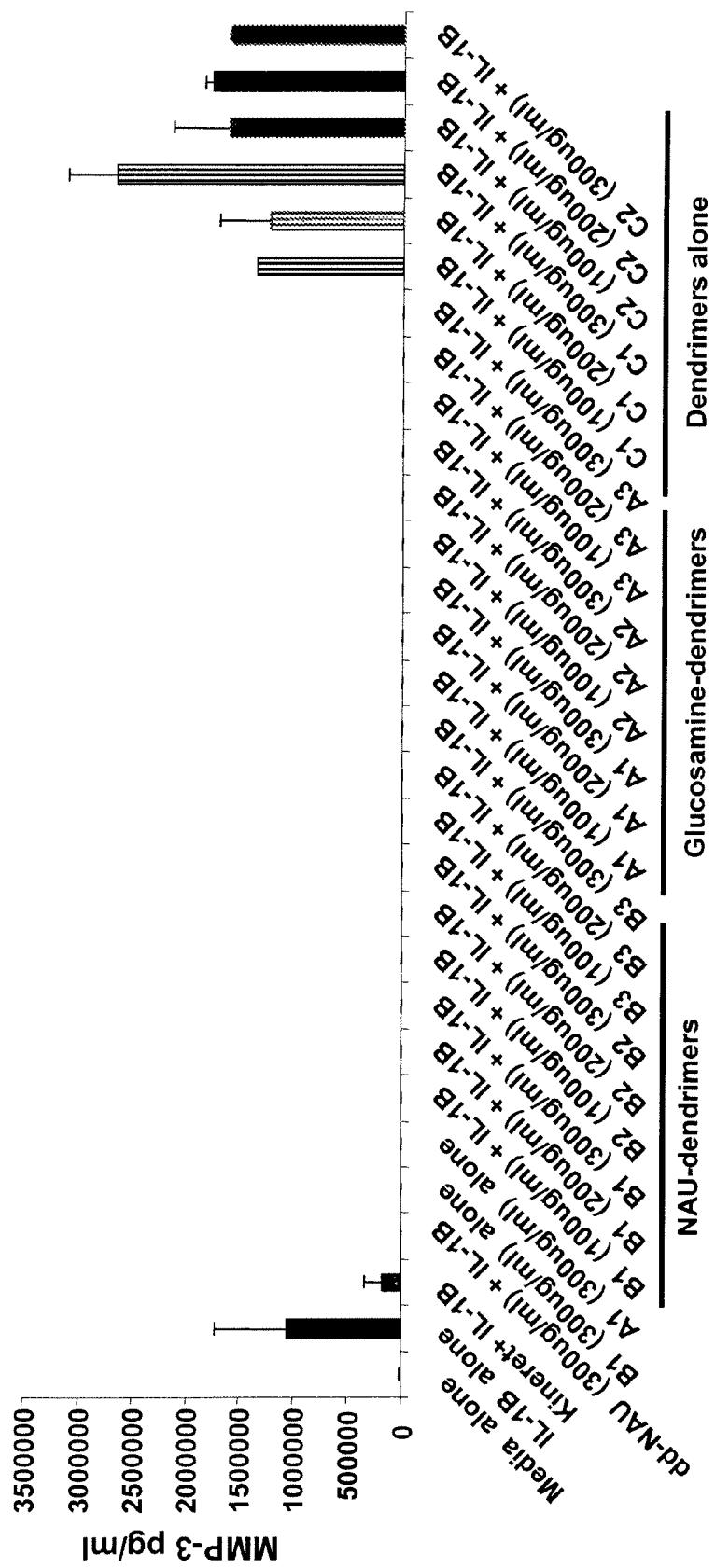
Figure 15: Effect of NAU- and Glucosamine dendrimers on MMP-3 production by human chondrocytes stimulated with IL-1β

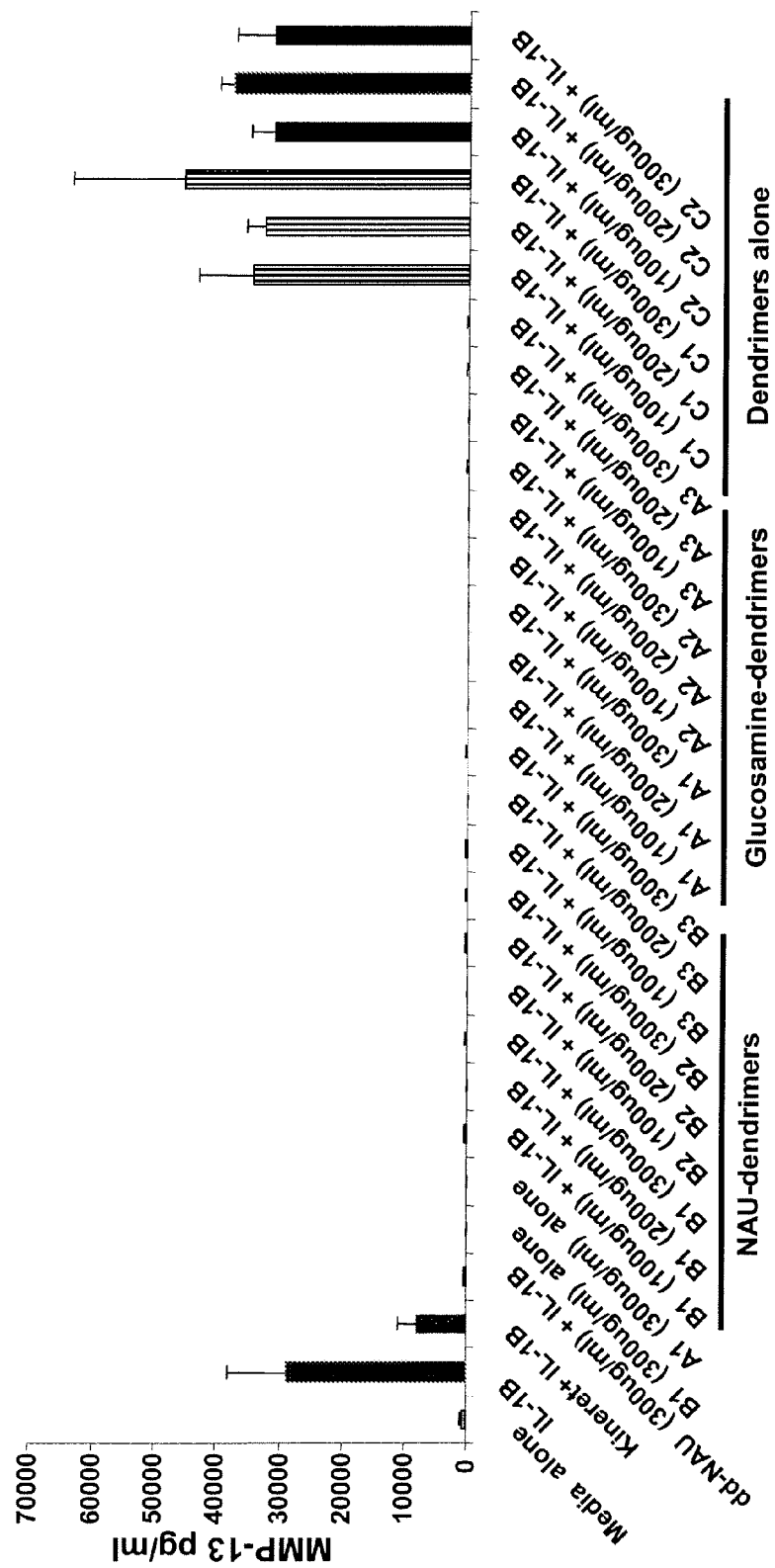
Figure 16: Effect of NAU- and Glucosamine dendrimers on MMP-13 production by human chondrocytes stimulated with IL-1β

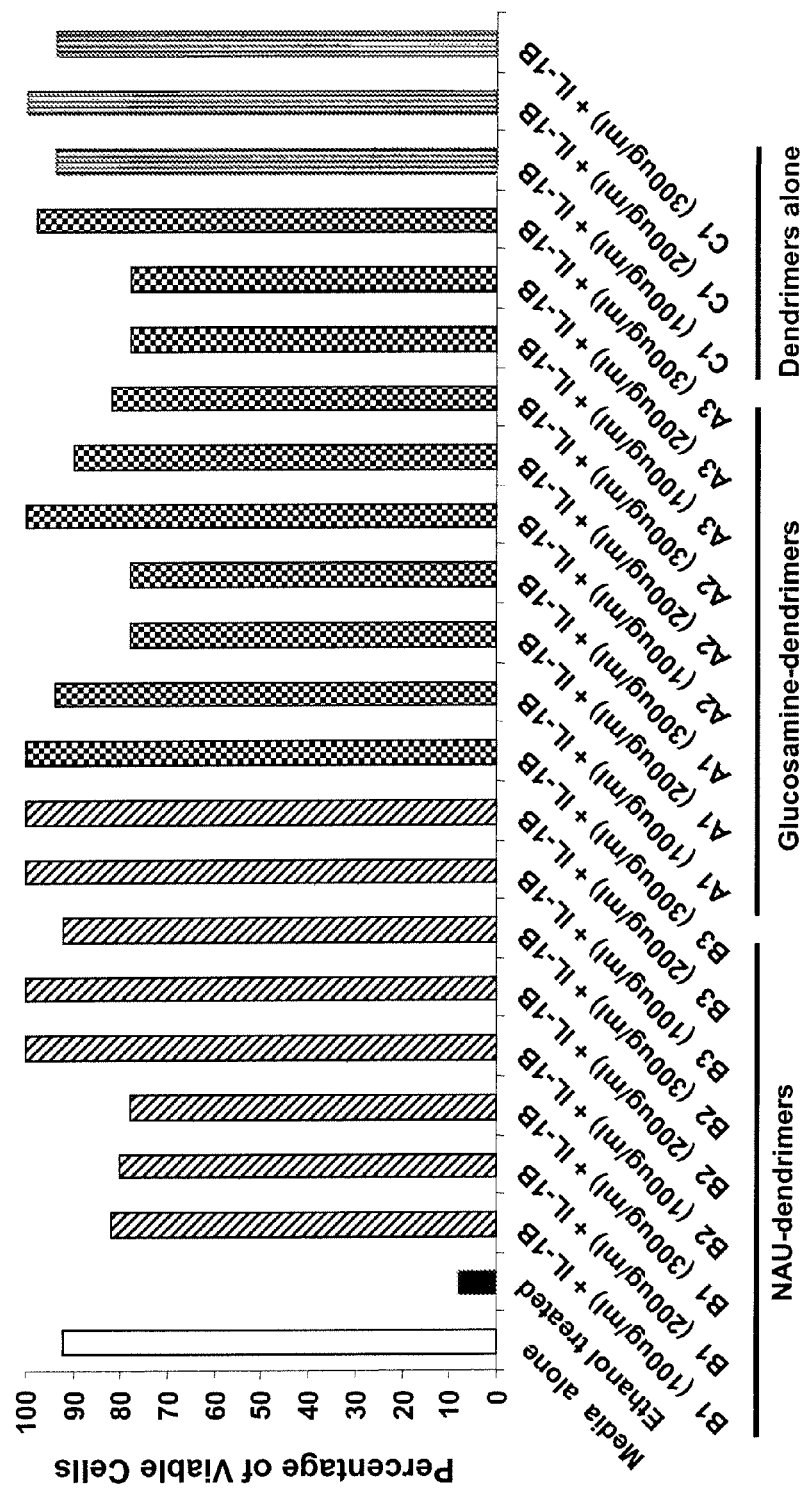
Figure 17: Effect of NAU- and Glucosamine dendrimers on cell viability in chondrocytes stimulated with IL-1β

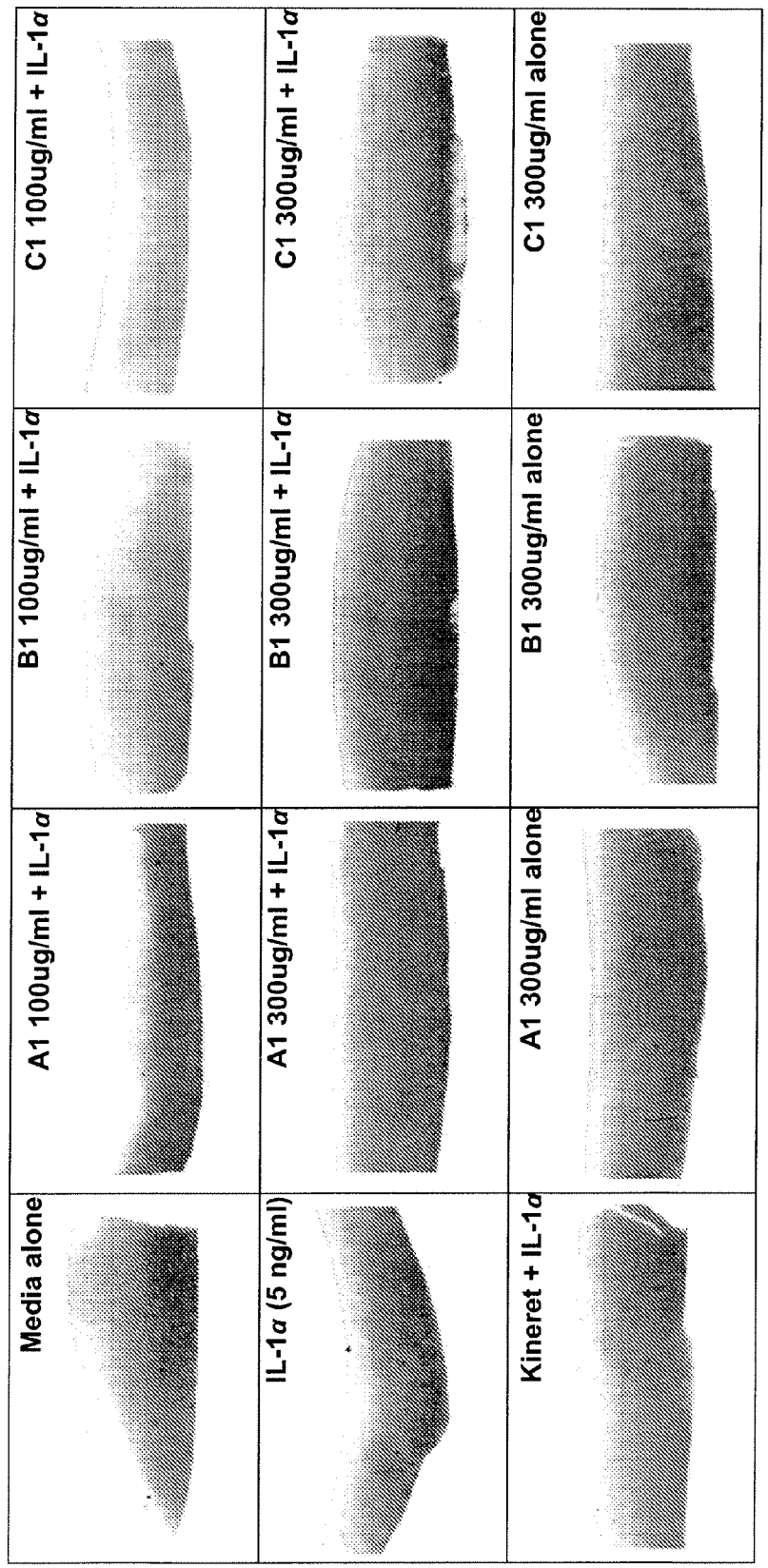
Figure 18: Effect of NAU- and Glucosamine dendrimers on IL-1α induced proteoglycan loss in bovine cartilage explant

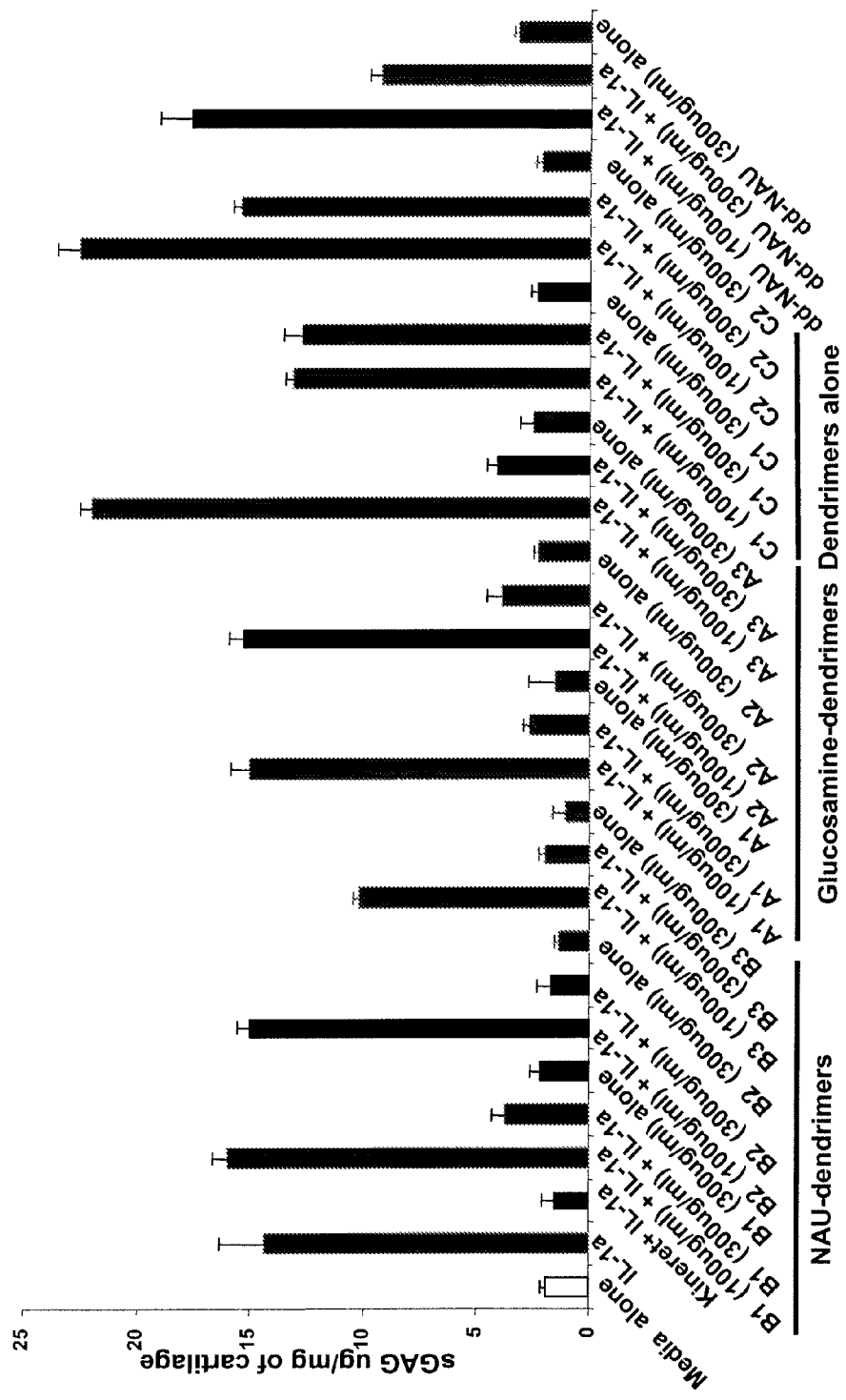
Figure 19: Effect of NAU- and Glucosamine dendrimers on IL-1α induced proteoglycan loss in bovine cartilage explant

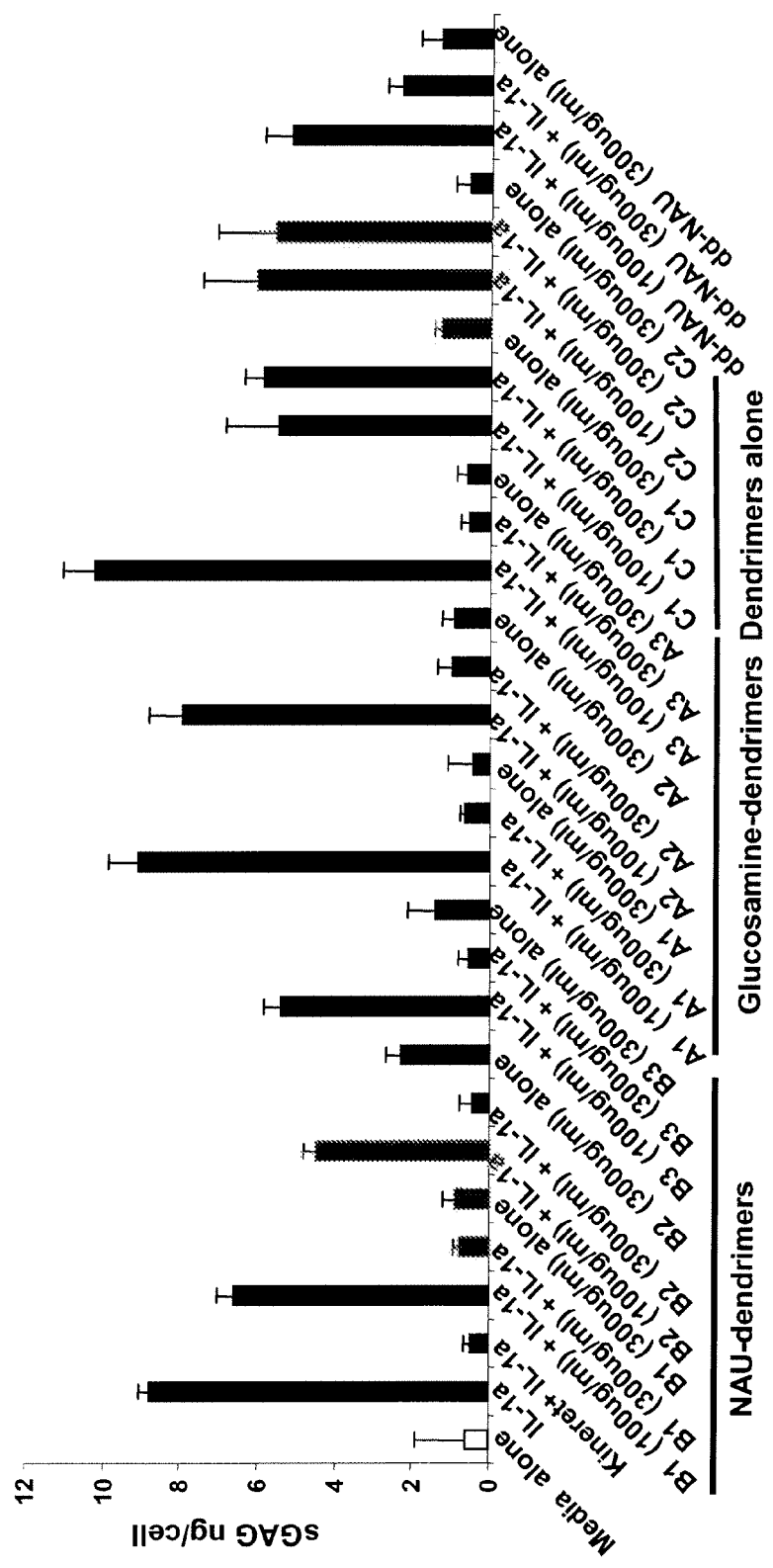
Figure 20: Effect of NAU- and Glucosamine dendrimers on IL-1α induced proteoglycan loss in bovine cartilage explant

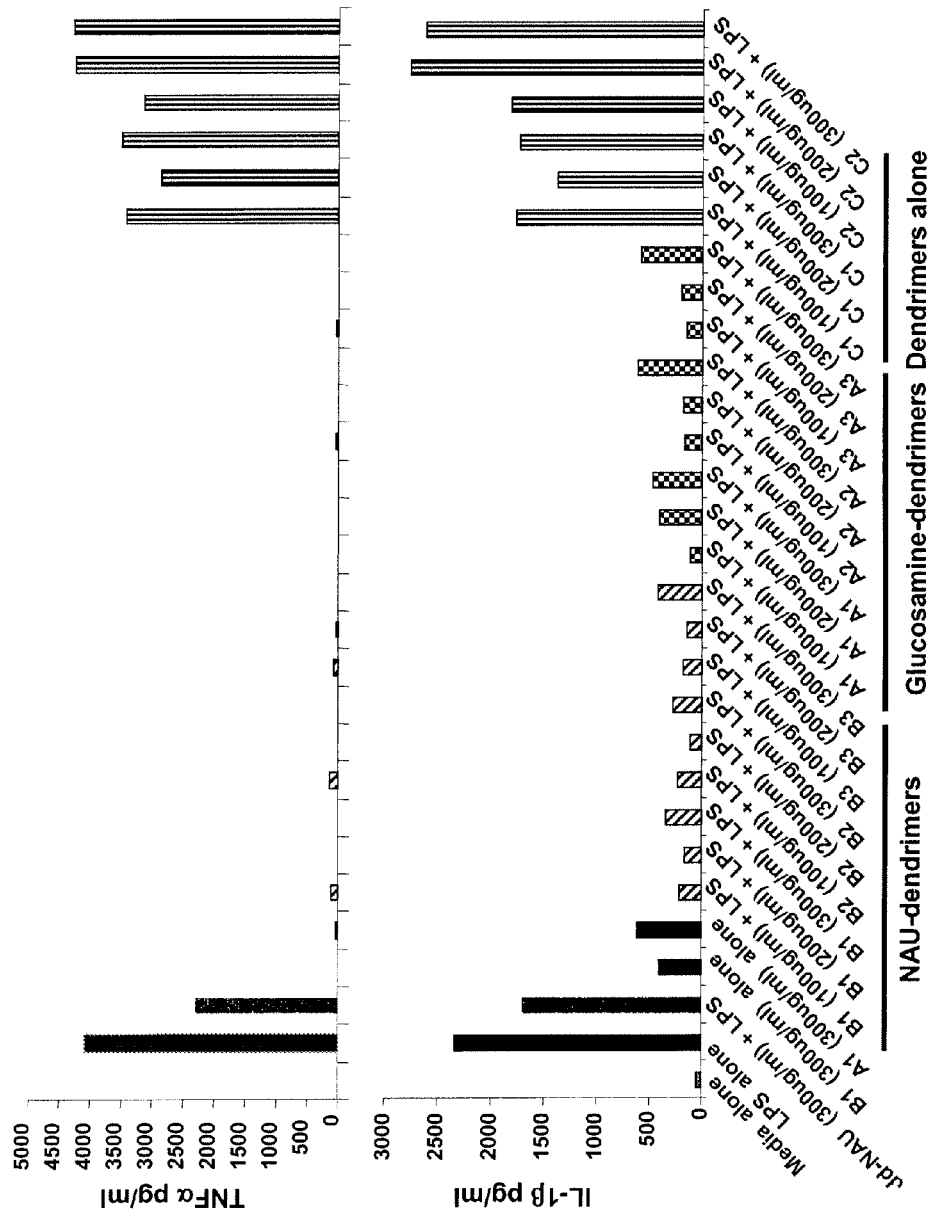
Figure 21: Effect of NAU- and Glucosamine dendrimers on TNF-α and IL-1β production by human macrophage cell line stimulated with LPS

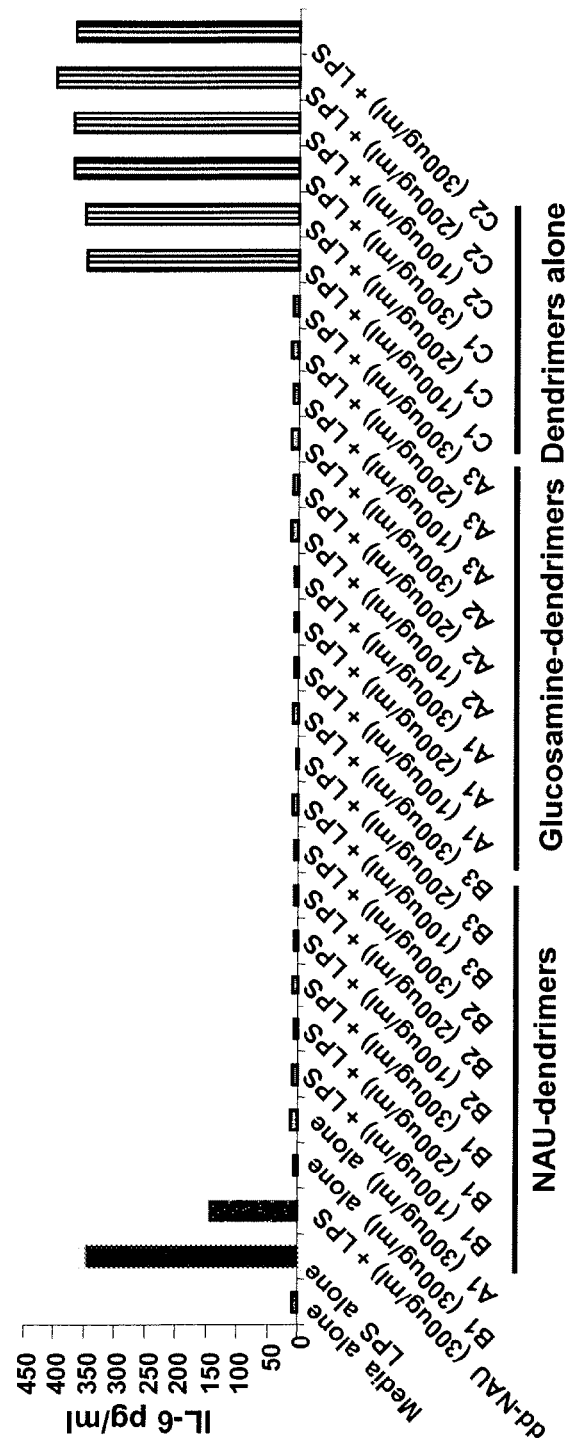
Figure 22: Effect of NAU- and Glucosamine dendrimers on IL-6 production by human macrophage cell line stimulated with LPS

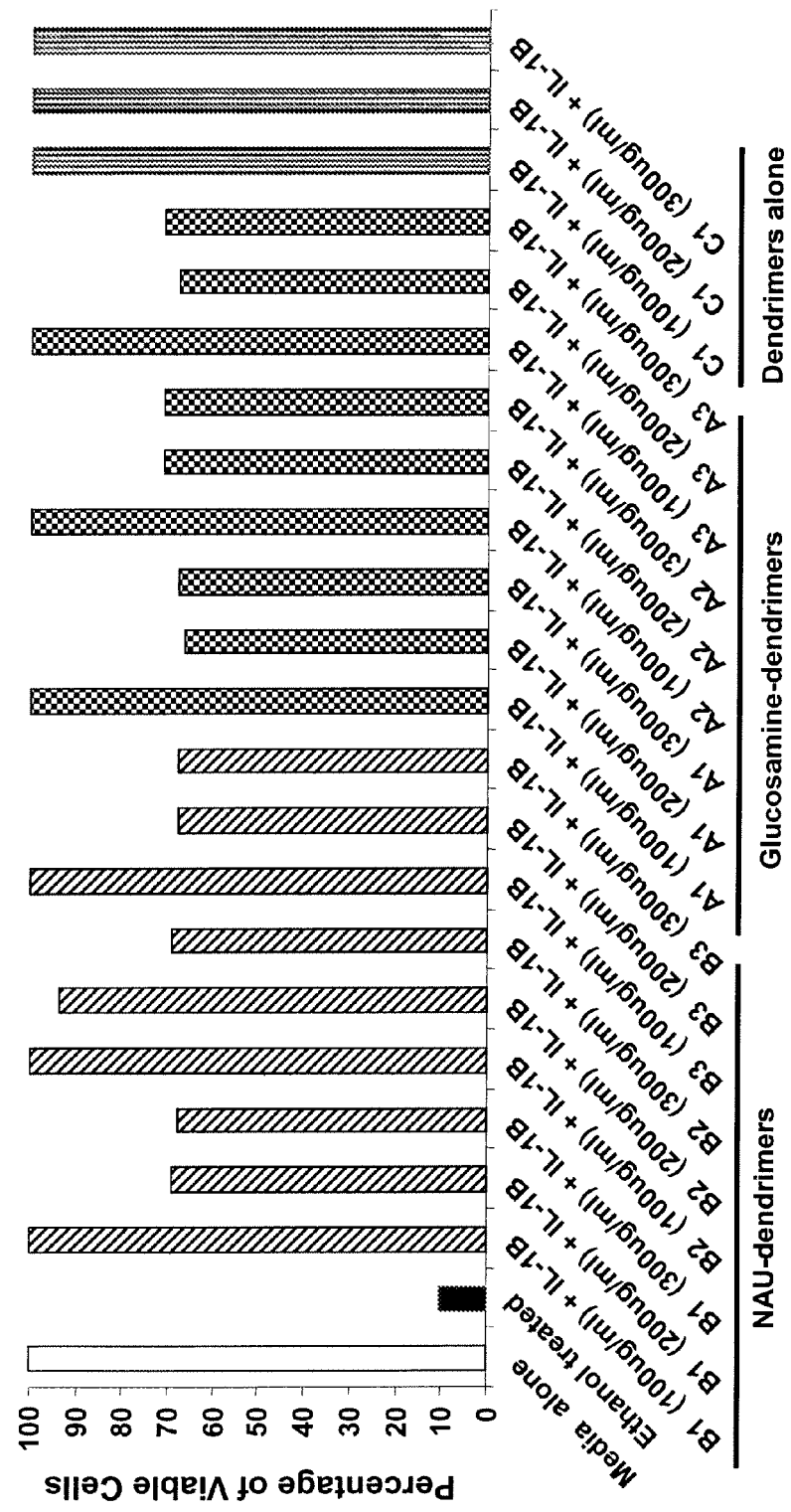
Figure 23: Effect of NAU- and Glucosamine dendrimers on cell viability in macrophage cell line stimulated with LPS

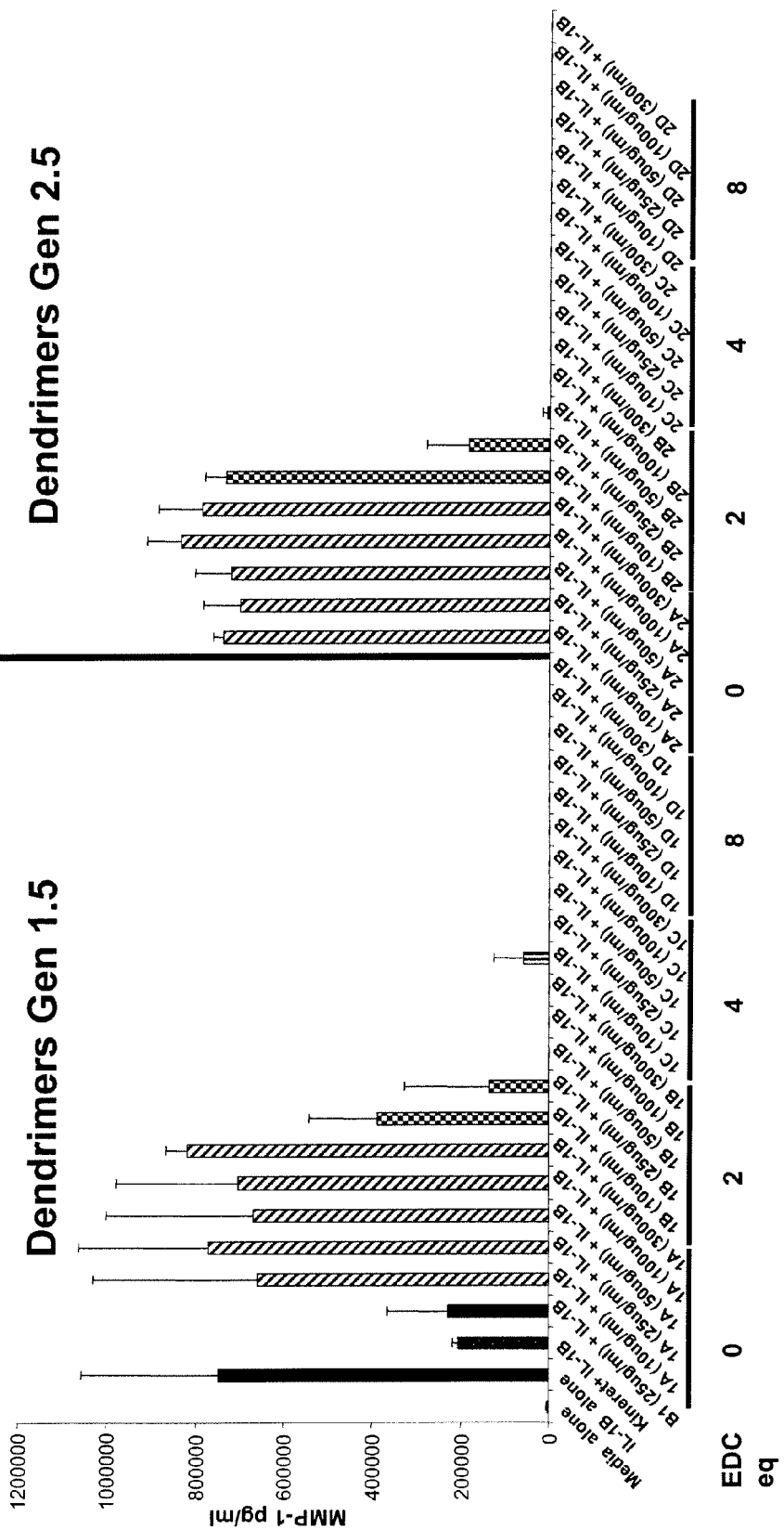
Figure 24: Effect of Lower generation dendrimers on MMP-1 production by human chondrocytes stimulated with IL-1β

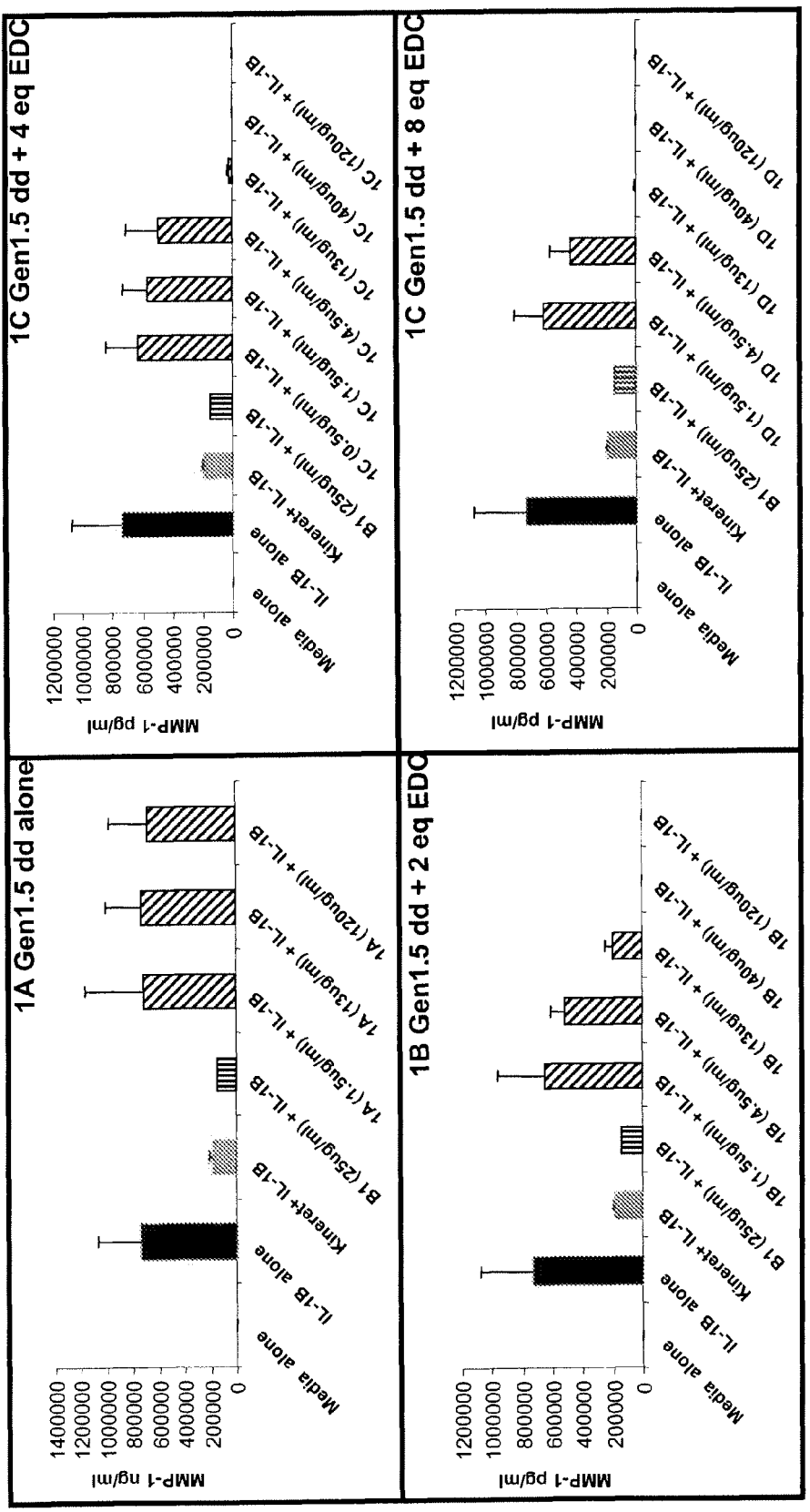
Figure 25: Effect of Lower Generation (1.5) dendrimers on MMP-1 production by human chondrocytes stimulated with IL-1β

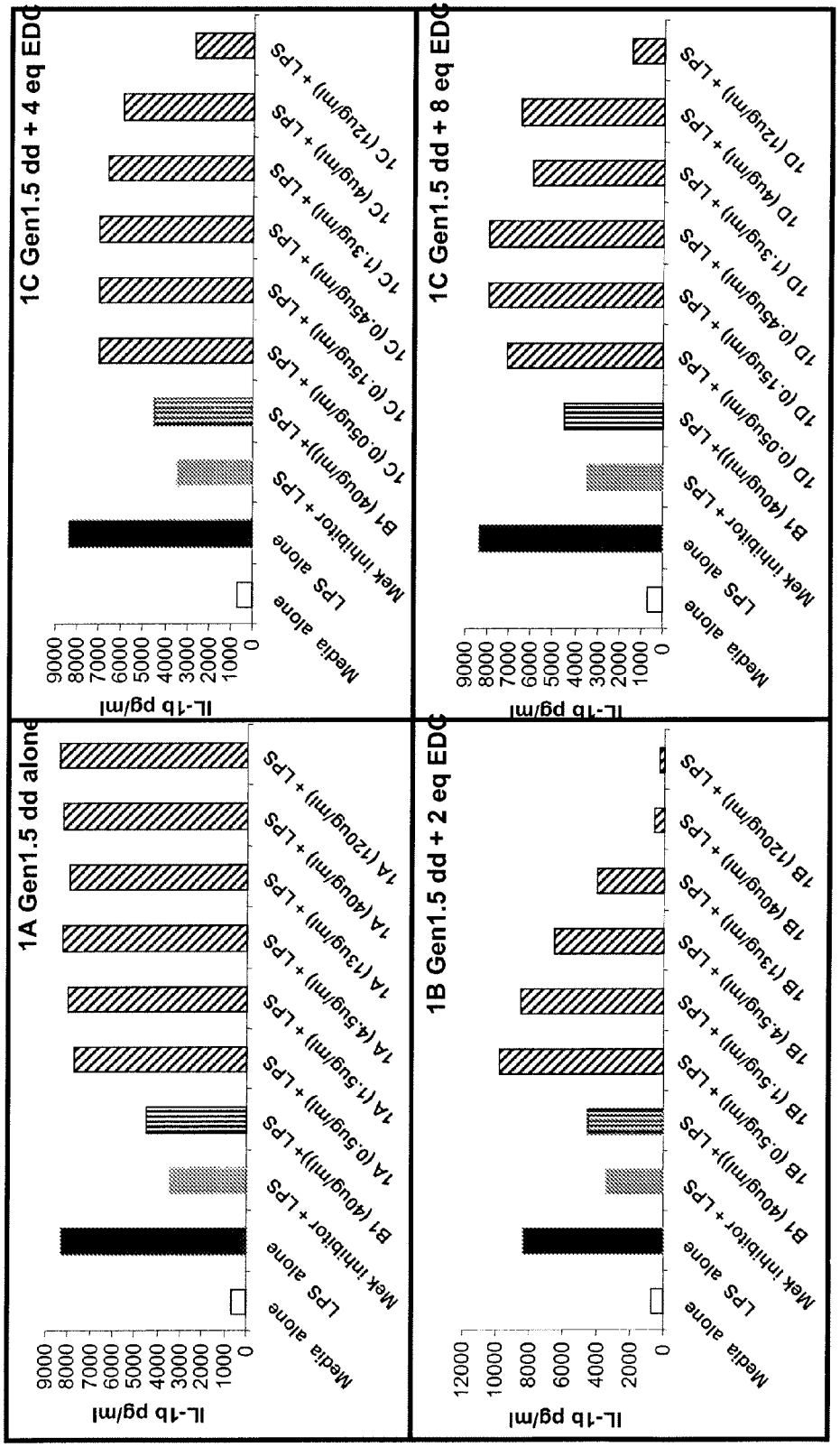
Figure 26: Effect of Lower Generation (1.5) dendrimers on IL-1β production by human THP-1 macrophage cell line stimulated with LPS

CHEMICALLY MODIFIED DENDRIMERS

CROSS REFERENCE TO RELATED APPLICATIONS

This application is a continuation application of U.S. application Ser. No. 14/151,165, filed on Jan. 9, 2014, which is a continuation application of U.S. application Ser. No. 12/142,266, filed on Jun. 19, 2008, now U.S. Pat. No. 8,658,148, which claims the benefit of U.S. Application No. 60/945,815, filed on Jun. 22, 2007, all of which are incorporated herein by reference in their entireties.

TECHNICAL FIELD

This invention relates to dendrimers, compositions comprising the dendrimers, and methods of use thereof, for example, in the treatment of inflammatory disorders such as arthritis.

BACKGROUND

There are many forms of arthritis, including rheumatoid arthritis, psoriatic arthritis, and osteoarthritis. The most common form of arthritis, osteoarthritis, is also known as degenerative joint disease and can occur following trauma to the joint, following an infection of the joint or simply as a result of aging. There is emerging evidence that abnormal anatomy may contribute to early development of osteoarthritis.

Osteoarthritis is a condition where low-grade inflammation can result in pain in the joints, for example, pain caused by wearing of the cartilage that covers and acts as a cushion inside joints. As the bone surfaces become less well protected by cartilage, a subject can experience pain upon simply bearing weight, for example walking or standing. Due to decreased movement caused by pain, regional muscles may atrophy, and ligaments may become more lax.

Arthritis is generally treated with NSAIDs, local injections of glucocorticoid or viscosupplements based on hyaluronan, salt of hyaluronic acid or derivative thereof, such as a solution of hyaluronan, and in some cases, with surgery, for example, joint replacement surgery. There is currently no cure for arthritis.

SUMMARY

Applicants have discovered that certain compounds can be used to treat MMP (e.g., MMP-1, -3, or -13) mediated disorders including inflammatory disorders, such as arthritis. The compounds are dendrimers having a plurality of terminal acyl urea moieties. The term "dendrimer," when used herein, refers to a polymer moiety comprised of branched repeating units that radiate out from a central atom, multifunctional moiety, or cluster of atoms. Each branched repeating unit terminates with a terminal moiety. An example of a dendrimer is shown below:

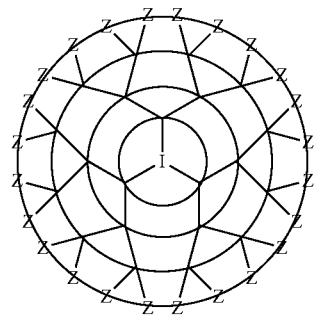

wherein I represents the central atom, multifunctional moiety, or cluster of atoms and Z represents the terminal moieties of the branched repeating units.

In one aspect, the invention features a dendrimer, the dendrimer comprising a plurality of branched repeating units radiating out from a central atom, multifunctional moiety, or cluster of atoms, wherein each repeating unit comprises a terminal moiety, and wherein at least about 5% of the terminal moieties include a urea of formula (I)

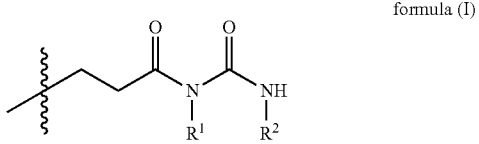

formula (I)

wherein each $R^1$ and $R^2$ is independently $C_1$-$C_6$ alkyl, $C_1$-$C_6$ alkenyl, cyclyl, aryl, heterocyclyl, heteroaryl, cyclylalkyl, arylalkyl, or heterocyclylalkyl, heteroarylalkyl; any of which are optionally substituted by $C_1$-$C_6$ alkyl, amino, $C_1$-$C_6$ alkylamino, $C_1$-$C_6$ dialkylamino, hydroxy, $C_1$-$C_6$ alkoxy, and wherein either of $R^1$ or $R^2$ independently optionally have a net charge;

⁝ indicates the point of attachment of the terminal moiety of formula (I) to the dendrimer; and wherein less than about 12% of the terminal moieties are covalently bound to a saccharide moiety.

In some embodiments, the dendrimer comprises a pharmaceutically acceptable salt.

In some embodiments, at least about 7% of the terminal moieties include a urea of formula (I) (e.g., at least about 8%, at least about 9%, at least about 10%, at least about 15%, at least about 20%, or at least about 25% of the terminal moieties include a urea of formula (I)).

In some embodiments, less than about 10% of the terminal moieties are covalently bound to a saccharide moiety (e.g., less than about 8%, less that about 6%, less that about 4%, or about 0% of the terminal moieties are covalently bound to a saccharide moiety).

In some embodiments, either of $R^1$ or $R^2$ has a net positive charge.

In some embodiments, $R^1$ and $R^2$ are both cyclohexyl.

In some embodiments, $R^1$ and $R^2$ are both isopropyl.

In some embodiments, one of $R^1$ and $R^2$ is ethyl and the other of $R^1$ and $R^2$ is dimethylaminopropyl.

In some embodiments, one of $R^1$ and $R^2$ is cyclohexyl and the other of $R^1$ and $R^2$ is morpholinoethyl.

In some embodiments, a terminal moiety includes a urea of formula (I) wherein each $R^1$ and $R^2$ is independently $C_1$-$C_6$ alkyl and one of $R^1$ and $R^2$ is substituted by $C_1$-$C_6$ dialkylamino, and wherein one of $R^1$ or $R^2$ has a positive net charge.

In some embodiments, a terminal moiety includes a urea of formula (I')

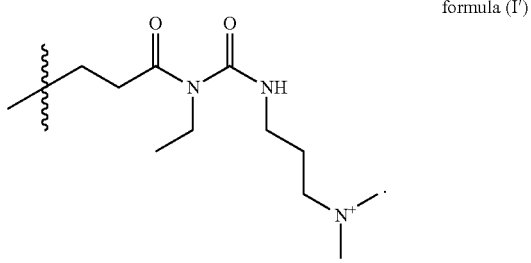 [SMILES: *CCC(=O)N(CC)C(=O)NCCC[NH+](C)C]

formula (I')

In some embodiments, a terminal moiety includes a urea of formula (I")

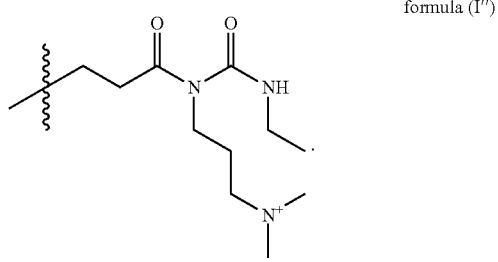 [SMILES: *CCC(=O)N(CCC[NH+](C)C)C(=O)NCC]

formula (I")

In some embodiments, at least about 5% of the terminal moieties include a urea of formula (I') or formula (I") or a combination thereof.

In some embodiments, the dendrimer is selected from the group consisting of a polyamidoamine dendrimer, a polypropylene dendrimer, a polyethyleneimine dendrimer, a carbohydrate based dendrimer, a peptide based dendrimer, a glycopeptide dendrimer, a metal containing dendrimer, a poly aryl amine dendrimer, a polyamide dendrimer, a poly (alkyl amine) dendrimer, a polyamido alcohol dendrimer, a cyano dendrimer, a polyether dendrimer, a polythioether dendrimer, a polysiloxane dendrimer, a dendritic aryl ester, a perchlorinated dendrimer, a catalytic center containing dendrimer, a silicon containing dendrimer, a phosphorus containing dendrimer, or a hydrocarbon dendrimer.

In some embodiments, the dendrimer is a polyamidoamine dendrimer.

In some embodiments, at least about 80% of the terminal moieties are terminated with a carboxylate group or with a functionality that can be chemically modified to produce a carboxylate moiety by suitable chemical reaction.

In some embodiments, the dendrimer is a polyamidoamine dendrimer wherein at least about 50% of the terminal moieties are terminated with a carboxylate group.

In some embodiments, the dendrimer is a polyamidoamine dendrimer of one of the following generations 0.5, 1.5, 2.5, 3.5, 4.5, 5.5, 6.5, 7.5, 8.5, or 9.5. In some embodiments, the dendrimer is a polyamidoamine dendrimer of generation 0.5, 1.5, 2.5, or 3.5 with a carboxylate terminal moiety.

In some embodiments, the dendrimer of formula (I) described herein, is made by reacting one or more terminal moieties of a starting dendrimer with a carbodiimide of formula (II) $R^1$—N=C=N—$R^2$, wherein $R^1$ and $R^2$ are defined above, to provide the dendrimer of formula (I).

In one aspect, the invention comprises a composition comprising the above-described dendrimer and a pharmaceutically acceptable excipient.

In some embodiments, each dendrimer within the composition comprises at least about 5% of the terminal moieties including a urea of formula (I).

In some embodiments, the dendrimers, in aggregate within the composition, comprise at least about 5% of the terminal moieties including a urea of formula (I).

In some embodiments, the composition further comprises an additional therapeutic agent. In some embodiments, the additional therapeutic agent is an anti-inflammatory agent or an analgesic. In some embodiments, the additional therapeutic agent is a salt of hyaluronic acid or a derivative thereof. In some embodiments, the additional therapeutic agent is a hylan. In some embodiments, the hyaluronic acid is a cross-linked salt of hyaluronic acid.

In one aspect, the invention features a method of treating or preventing arthritis or reducing a symptom associated with arthritis, the method comprising administering to a subject an effective amount of the above-described dendrimer.

In some embodiments, the method comprises preventing or alleviating one or more symptoms associated with arthritis or extending the amount of time prior to the onset of one or more symptoms associated with arthritis.

In some embodiments, the method comprises treating a subject exhibiting one or more symptoms associated with arthritis. In some embodiments, the arthritis is osteoarthritis. In some embodiments, the arthritis is rheumatoid arthritis.

In some embodiments, the method comprises administering an additional therapeutic agent. In some embodiments, the additional therapeutic agent is an anti-inflammatory agent or an analgesic. In some embodiments, the additional therapeutic agent is a salt of hyaluronic acid or a derivative thereof. In some embodiments, the additional therapeutic agent is hylan. In some embodiments, the hyaluronic acid is a cross-linked hyaluronic acid. In some embodiments, the additional therapeutic agent is a mixture of a soluble and crosslinked salt of HA such as a mixture of hylan A and hylan B/e.g. Synvisc®.

In some embodiments, the additional therapeutic agent is co-administered with the dendrimer. In some embodiments, the additional therapeutic agent is administered before or after administration of the dendrimer.

In some embodiments, the dendrimer is a component in a pharmaceutical composition. In some embodiments, the pharmaceutical composition comprises a pharmaceutically acceptable excipient. In some embodiments, the concentration of the dendrimer within the composition is from about 1 to about 1000 μg/mL.

In some embodiments, the dendrimer is administered via injection. In some embodiments, the dendrimer is administered parenterally. In some embodiments, the dendrimer is administered via intraarticular injection.

In some embodiments, the subject is a mammal, for example, a human.

In one aspect, the invention features a method of making the above-described dendrimer; the method comprising reacting a dendrimer comprising a plurality of terminal carboxylic acid moieties with a carbodiimide, wherein the carbodiimide is substituted with $R^1$ and $R^2$ as defined anywhere herein, thereby making the dendrimer of formula (I).

In some embodiments, the reaction is performed in aqueous solution. In some embodiments, the aqueous solution has a pH of from about 4.0 to about 7.0, for example, a pH of from about 4.5 to about 5.0.

In some embodiments, the reaction is performed in a mixture of water and organic solvent. In some embodiments, the organic solvent comprises from about 5% to less than about 100% by volume. In some embodiments, the organic solvent comprises about 50% by volume. In some embodiments, the organic solvent is selected from the group consisting of acetonitrile, tetrahydrofuran, or N-methylpyrrolidone.

In some embodiments, the reaction occurs at a temperature of from about 4° C. to about 35° C., for example, at a temperature of from about 20° C. to about 35° C.

In some embodiments, the reaction is maintained for from about 12 to about 24 hours.

In some embodiments, the method comprises reacting from about 0.5 to about 10 equivalents of carbodiimide per terminal carboxyl moiety, for example, from about 1 to about 4 equivalents of carbodiimide per terminal carboxyl moiety.

In some embodiments, the carbodiimide is selected from the group consisting of N-(3-Dimethylaminopropyl)-N'-ethylcarbodiimide, N,N'-Dicyclohexylcarbodiimide, N,N'-Diisopropylcarbodiimide, 1-[3-(Dimethylamino)propyl]-3-ethylcarbodiimide methiodide, and N-Cyclohexyl-N'-(2-morpholinoethyl)carbodiimide methyl-p-toluenesulfonate, preferably N-(3-Dimethylaminopropyl)-N'-ethylcarbodiimide.

In some embodiments, the method comprises reacting from about 2 equivalents of N-(3-Dimethylaminopropyl)-N'-ethylcarbodiimide per terminal carboxyl moiety.

In some embodiments, the method further comprises purifying the reaction product, for example, by dialysis. In some embodiments, the dialysis is performed at a temperature of from between about 2° C. and about 8° C. In some embodiments, the method further comprises lyophilizing the dialysed product. In some embodiments, the reaction product is purified by size exclusion chromatography.

In another aspect, the invention features a dendrimer, the dendrimer comprising a plurality of branched repeating units radiating out from a central atom, multifunctional moiety, or cluster of atoms, wherein each repeating unit comprises a terminal moiety, and wherein at least one of the terminal moieties include a urea of formula (I)

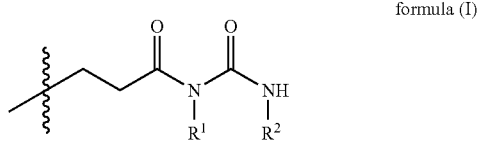

formula (I)

in which
each $R^1$ and $R^2$ is independently $C_1$-$C_6$ alkyl, $C_1$-$C_6$ alkenyl, cyclyl, aryl, heterocyclyl, heteroaryl, cyclylalkyl, arylalkyl, or heterocyclylalkyl, heteroarylalkyl; any of which are optionally substituted by $C_1$-$C_6$ alkyl, amino, $C_1$-$C_6$ alkylamino, $C_1$-$C_6$ dialkylamino, hydroxy, $C_1$-$C_6$ alkoxy, and wherein either of $R^1$ or $R^2$ independently optionally have a net charge;

⌇ indicates the point of attachment of the terminal moiety of formula (I) to the dendrimer; and wherein less than about 12% of the terminal moieties are covalently bound to a saccharide moiety.

In some embodiments, 0% of the terminal moieties are covalently bound to a saccharide moiety.

In a further aspect, the invention features a dendrimer, the dendrimer comprising a plurality of branched repeating units comprising a plurality of terminal moieties radiating out from a central atom, multifunctional moiety, or cluster of atoms, wherein the dendrimer is made by reacting at least one terminal moiety with a carbodiimide to provide a terminal modified dendrimer.

In certain embodiments, the carbodiimide is of formula (II)

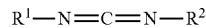

Formula (II)

wherein
each $R^1$ and $R^2$ is independently $C_1$-$C_6$ alkyl, $C_1$-$C_6$ alkenyl, cyclyl, aryl, heterocyclyl heteroaryl, cyclylalkyl, arylalkyl, or heterocyclylalkyl, heteroarylalkyl; any of which are optionally substituted by $C_1$-$C_6$ alkyl, amino, $C_1$-$C_6$ alkylamino, $C_1$-$C_6$ dialkylamino, hydroxy, $C_1$-$C_6$ alkoxy, and wherein either of $R^1$ or $R^2$ independently optionally have a net charge.

In some embodiments, the reaction is substantially free of saccharide moieties.

In some embodiments, at least 12% of the terminal moieties react with the carbodiimide.

As used herein, the term "treat" or "treatment" is defined as the application or administration of a dendrimer, alone or in combination with, a second compound to a subject, e.g., a patient, or application or administration of the compound to an isolated tissue or cell, e.g., cell line, from a subject, e.g., a patient, who has a disorder (e.g., a disorder as described herein), a symptom of a disorder, or a predisposition toward a disorder, with the purpose to cure, heal, alleviate, relieve, alter, remedy, ameliorate, improve or affect the disorder, one or more symptoms of the disorder or the predisposition toward the disorder (e.g., to prevent at least one symptom of the disorder or to delay onset of at least one symptom of the disorder).

As used herein, an amount of a compound (e.g., a dendrimer) effective to treat a disorder, or a "therapeutically effective amount" refers to an amount of the compound (e.g., a dendrimer) which is effective, upon single or multiple dose administration to a subject, in treating a cell, or in curing, alleviating, relieving or improving a subject with a disorder beyond that expected in the absence of such treatment.

As used herein, an amount of a compound (e.g., a dendrimer) effective to prevent a disorder, or a "a prophylactically effective amount" of the compound (e.g., a dendrimer) refers to an amount effective, upon single- or multiple-dose administration to the subject, in preventing or delaying the occurrence of the onset or recurrence of a disorder or a symptom of the disorder.

As used herein, the term "subject" is intended to include human and non-human animals. Exemplary human subjects include a human patient having a disorder, e.g., a disorder described herein or a normal subject. The term "non-human animals" of the invention includes all vertebrates, e.g., non-mammals (such as chickens, amphibians, reptiles) and mammals, such as non-human primates, domesticated and/or agriculturally useful animals, e.g., sheep, dog, cat, cow, pig, horse, etc.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a bar graph depicting the effect of dd-NAU and dd-Gln on Levels of Active MMP-1 in chondrocytes stimulated with IL-1β.

FIG. 2 is a bar graph depicting the real-time quantitative PCR analysis of MMP-1 RNA from cells treated with dd-NAU and dd-Gln.

FIG. 3 is a bar graph depicting the real-time quantitative PCR analysis of GAPDH RNA from cells treated with dd-NAU and dd-Gln.

FIG. 4 is a bar graph depicting the real-time quantitative PCR analysis of MMP-1 normalized to GAPDH.

FIG. 5 is a bar graph depicting the effect of dd-NAU and dd-Gln on levels of active MMP-3 in chondrocytes stimulated with IL-1β.

FIG. 6 is a bar graph depicting the real-time quantitative PCR analysis of MMP-3 RNA from cells treated with dd-NAU and dd-Gln.

FIG. 7 is a bar graph depicting the real-time quantitative PCR analysis of MMP-3 normalized to GAPDH.

FIG. 8 is a bar graph depicting the effects of dd-NAU and dd-Gln on levels of active MMP-13 in chondrocytes stimulated with IL-1β.

FIG. 9 is a bar graph depicting the real-time quantitative PCR analysis of MMP-3 RNA from cells treated with dd-NAU and dd-Gln.

FIG. 10 is a bar graph depicting the real-time quantitative PCR analysis of MMP-13 normalized to GAPDH.

FIG. 11 depicts histological analysis of bovine cartilage explants.

FIG. 12 is a bar graph depicting the chondroprotective role of dd-NAU (Normalized to Wet Weight).

FIG. 13 is a bar graph depicting the chondroprotective role of dd-NAU (Normalized to DNA).

FIG. 14 is a bar graph depicting the effect of NAU- and glucosamine dendrimers on MMP-1 production by human chondrocytes stimulated with IL-1β.

FIG. 15 is a bar graph depicting the effect of NAU- and glucosamine dendrimers on MMP-3 production by human chondrocytes stimulated with IL-1β.

FIG. 16 is a bar graph depicting the effect of NAU- and glucosamine dendrimers on MMP-13 production by human chondrocytes stimulated with IL-1β.

FIG. 17 is a bar graph depicting the effect of NAU- and glucosamine dendrimers on cell viability in chondrocytes stimulated with IL-1β.

FIG. 18 are histograms depicting the effect of NAU- and glucosamine dendrimers on IL-1α induced proteoglycan loss in bovine cartilage explant.

FIG. 19 is a bar graph depicting the effect of NAU- and glucosamine dendrimers on IL-1α induced proteoglycan loss in bovine cartilage explant.

FIG. 20 is a bar graph depicting the effect of NAU- and glucosamine dendrimers on IL-1α induced proteoglycan loss in bovine cartilage explant.

FIG. 21 are bar graphs depicting the effect of NAU- and glucosamine dendrimers on TNF-α and IL-1β production by human macrophage cell line stimulated with LPS.

FIG. 22 is a bar graph depicting the effect of NAU- and glucosamine dendrimers on IL-6 production by human macrophage cell line stimulated with LPS.

FIG. 23 is a bar graph depicting the effect of NAU- and glucosamine dendrimers on cell viability in macrophage cell line stimulated with LPS.

FIG. 24 is a bar graph depicting the effect of Lower generation dendrimers on MMP-1 production by human chondrocytes stimulated with IL-1β.

FIG. 25 are bar graphs depicting the effect of Lower Generation (1.5) dendrimers on MMP-1 production by human chondrocytes stimulated with IL-1β.

FIG. 26 are bar graphs depicting the effect of Lower Generation (1.5) dendrimers on IL-1b production by human THP-1 macrophage cell line stimulated with LPS.

DETAILED DESCRIPTION

Dendrimer Compounds

Dendrimers are well-defined macromolecules that have a specific size, shape, and chemical functionality. A dendrimer is a branched monodisperse macromolecular compound. Structurally dendrimers are highly branched macromolecules that can be subdivided into three architectural components: a central core branched cell, interior branch cell and branch cell possessing surface groups. They are generally synthesized through a stepwise repetitive reaction sequence. The dendrimers described herein include a plurality of terminal moieties comprising an N-acyl urea moiety as provided below:

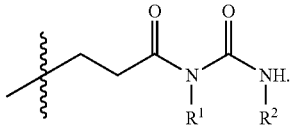

Each $R^1$ and $R^2$ is independently $C_1$-$C_6$ alkyl, $C_1$-$C_6$ alkenyl, cyclyl, aryl, heterocyclyl, heteroaryl, cyclylalkyl, arylalkyl, or heterocyclylalkyl, heteroarylalkyl; any of which are optionally substituted by $C_1$-$C_6$ alkyl, amino, $C_1$-$C_6$ alkylamino, $C_1$-$C_6$ dialkylamino, hydroxy, $C_1$-$C_6$ alkoxy, and wherein either of $R^1$ or $R^2$ independently optionally have a net charge; ⸹ indicates the point of attachment of the terminal moiety of formula (I) to the dendrimer. In preferred embodiments, at least 5% of the terminal moieties have the structure provided above (e.g., at least about 7%, 8%, 9%, 10%, 15%, 20%, or 25%). In some embodiments, one or more terminal moieties of the dendrimer not having the formula above are carboxy moieties (for example, all of the terminal moieties not having the formula above are carboxy moieties). The dendrimers described herein have less than 12% of the terminal moieties covalently bound to a saccharide moiety, for example Gln (e.g., less than about 10%, 8%, 6%, 4%, or 1%). In some preferred embodiments, none of the terminal moieties are covalently bound to a saccharide moiety.

In some preferred embodiments at least one of $R^1$ and $R^2$ includes a nitrogen moiety (e.g., an alkyl substituted with an amino moiety or a nitrogen containing heterocyclic moiety such as piperidine or morpholine). For example, one of $R^1$ and $R^2$ has a net positive charge.

In some preferred embodiments one of $R^1$ and $R^2$ is an unsubstituted alkyl moiety (e.g., $C_1$-$C_6$ alkyl, preferably $C_1$-$C_3$ alkyl, e.g., methyl or ethyl) and the other of $R^1$ or $R^2$ is an alkyl substituted with an amino moiety (e.g., a dialkyl amino moiety such as dimethylamino). For example, one of $R^1$ and $R^2$ is ethyl and the other of $R^1$ or $R^2$ is dimethylaminopropyl or one of $R^1$ and $R^2$ is cyclohexyl and the other of $R^1$ and $R^2$ is morpholinoethyl. In some instances where one or $R^1$ and $R^2$ includes a nitrogen moiety the terminal moiety forms a salt (e.g., with the cationic amine nitrogen, for example, to produce a quaternary ammonium).

Some preferred terminal moieties are provided below:

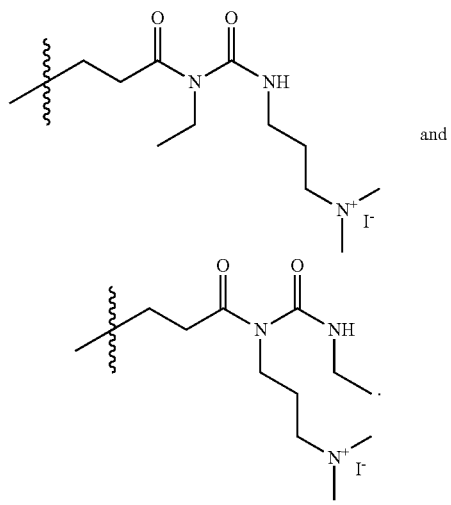

In some embodiments neither of $R^1$ or $R^2$ includes a heteroatom substituent. For example, in some embodiments, $R^1$ and $R^2$ are both isopropyl or $R^1$ and $R^2$ are both cyclohexyl.

Examples of dendrimers include the following: a polyamidoamine dendrimer, a polypropylene dendrimer, a polyethyleneimine dendrimer, a carbohydrate based dendrimer, a peptide based dendrimer, a glycopeptide dendrimer, a metal containing dendrimer, a poly aryl amine dendrimer, a polyamide dendrimer, a poly (alkyl amine) dendrimer, a polyamido alcohol dendrimer, a cyano dendrimer, a polyether dendrimer, a polythioether dendrimer, a polysiloxane dendrimer, a dendritic aryl ester, a perchlorinated dendrimer, a catalytic center containing dendrimer, a silicon containing dendrimer, a phosphorus containing dendrimer, or a hydrocarbon dendrimer. The preferred dendrimers include a polyvalent core covalently bonded to at least two dendritic branches. Particularly preferred dendrimers are dendrimers where the core and interiors branches are derived from cells. Exemplary preferred embodiments are polyamidoamine (PAMAM) dendrimers (e.g., generation 1.5, 2.5, or 3.5), PAMAM (EDA) dendrimers, polylysine dendrimers, polypropylene dendrimer and the branch cell containing surface group carboxylic terminal moieties.

In some preferred embodiments, the dendrimer is a PAMAM generation 3.5 dendrimer wherein from about 8 to about 15% of the terminal moieties have one of the following structures:

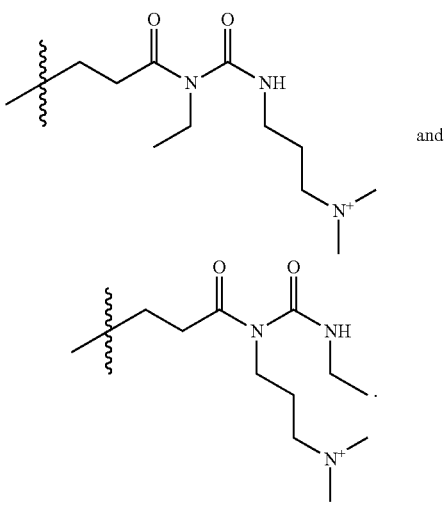

Methods of Making Dendrimers

The preparation of dendrimers is discussed in U.S. Pat. Nos. 4,507,466, 4,558,120, 4,568,737 and 4,587,329 (PAMAM dendrimers), as well as in U.S. Pat. Nos. 4,289,872 and 4,410,688 (lysine based dendrimer). International Patent Publications Nos. WO 88/01178, WO 88/01179 and WO 88/01180 disclose conjugates or associates of dendrimer with another material such as a carried pharmaceutical material.

The dendrimers described herein are prepared by reacting at least a portion of the terminal moieties (e.g., terminal carboxy moieties) with a reactant such as a carbodiimide, which produces some N-acyl urea. In some embodiments, not all of the terminal moieties react with the reactant (e.g., carbodiimide (i.e., "CDI")) to provide an N-acyl urea, but instead remain unreacted carboxy moieties. Thus, the dendrimers described herein generally include terminal moieties with at least two structural variations (e.g., the starting structure of the terminal moiety and the structure of the reacted product (i.e., N-acyl urea)). In instances where the dendrimer is reacted with an unsymmetrical reactant (e.g., an unsymmetrical carbodiimide), then the dendrimer can include three different structural variations on the terminal moieties. In some embodiments, the starting terminal moiety is reacted with a CDI to provide yet a modified terminal moiety other than the starting material or the final N-acyl urea.

Exemplary carbodiimide reactants include N-(3-Dimethylaminopropyl)-N'-ethylcarbodiimide, N,N'-Dicyclohexylcarbodiimide, N,N'-Diisopropylcarbodiimide, 1-[3-(Dimethylamino)propyl]-3-ethylcarbodiimide methiodide, and N-Cyclohexyl-N'-(2-morpholinoethyl)carbodiimide methyl-p-toluenesulfonate. In some preferred embodiments, N-(3-Dimethylaminopropyl)-N'-ethylcarbodiimide is reacted with the dendrimer.

The degree of reaction of the reactant (e.g., carbodiimide) with the starting terminal moieties can be controlled or varied by modification of the reaction conditions. For example, an increase in molar equivalents of carbodiimide to terminal carboxyl moiety generally increases the relative amount of terminal moieties on the starting dendrimer (e.g., carboxy moieties) that are converted (e.g., to N-acyl urea moieties). Exemplary ratios are from about 0.5 to about 10 molar equivalents of carbodiimide to terminal moieties (e.g., from about 1 to about 4, e.g., about 2 or about 4). In general, at least one terminal moiety is reacted.

The reaction can be further controlled with conditions such as temperature, pH, solvent and time. The dendrimers are generally reacted with starting reagent at a temperature of from about 4° C. to about 35° C. (e.g., from about 20° C. to about 35° C.). In instances where the dendrimers are formed using a carbodiimide, the pH of the reaction is generally from about 4.5 to about 7.0, e.g., from about 4.5 to about 5.0. The reactions are generally performed in an aqueous solution. In some embodiments, the reactions are performed in a mixture of water and an organic solvent, for example, acetonitrile, tetrahydrofuran, or N-methylpyrrolidone. In general, the starting materials are subjected to reaction conditions for about 12-24 hours.

After the starting dendrimer has been treated with reagent, the reaction product is generally purified, for example, using precipitation, chromatography (e.g., ion-exchange), dialysis or filtration. The purified product can be further processed, for example lyophilized.

Dendrimer products can be characterized by various analytical techniques to determine the degree of terminal modification. These assays include HPLC, RPLC, UPLC, CZE, and CGE separation techniques in combination with detection methods using MALDI-TOF, LIF, UV, CAD or ESI-MS. Additionally, 1H NMR analysis is capable of characterizing the dendrimer products.

Methods of Using Dendrimers

In some embodiments, a dendrimer described herein is administered to a subject to reduce one or more symptoms or manifestations of arthritis. For example, a dendrimer described herein can modify (e.g., reduce) and pain and/or other symptoms associated with arthritis. Clinical endpoints the can be used to evaluate the modification of one or more of pain or symptoms include X-ray (e.g., evaluation of Joint space narrowing), MM (for evaluation of synovitis (inflammation cell infiltration), evaluation of cartilage volume and proteoglycan content), Arthroscopy/Ultrasonography (evaluation of visualize cartilage lesion), Biomarkers (evaluation of serum, urine and synovial fluid analyzed for collagen type I and II breakdown products, MMP-1, 3, 13, IL-1, IL-6, TNFa, COMP-1) and evaluation of Pain scores for symptoms.

The dendrimers described herein have been found to exhibit activity against MMP activity (e.g., MMP-1, -3, and -13), which has been implicated in arthritis (e.g., osteoarthritis or rheumatoid arthritis). The dendrimers described herein can be used to treat, prevent, or delay the onset of an inflammatory disorder such as arthritis (e.g., osteoarthritis or rheumatoid arthritis).

The dendrimers described herein can, for example, be administered by injection, intravenously, intraarterially, subdermally, intraperitoneally, intramuscularly, subcutaneously, or intraarticularly (e.g., in the joint space); or orally, buccally, nasally, transmucosally, topically, in an ophthalmic preparation, or by inhalation, with a dosage ranging from about 0.001 to about 100 mg/kg of body weight, e.g., between 0.001-1 mg/kg, 1-100 mg/kg, or 0.01-5 mg/kg, every 4 to 120 hours, e.g., about every 6, 8, 12, 24, 48, or 72 hours, or according to the requirements of the particular dendrimer. The methods herein contemplate administration of an effective amount of dendrimer or dendrimer composition to achieve the desired or stated effect (e.g., reduction of pain and/or inflammation in a subject). Typically, the pharmaceutical compositions of this invention will be administered from about 1 to about 6 times per day. Alternatively, the dendrimers can be administered as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific dendrimer employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a dendrimer, composition or combination of this invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms.

In some embodiments a dendrimer described herein is administered with another therapeutic agent, for example an anti-inflammatory agent or an analgesic. As used herein, "co-administration" or "combination therapy" means that two or more agents are administered to a subject at the same time or within an interval such that there is an overlap of an effect of each agent on the patient. In some embodiments, agents are administered within 15, 10, 5, or 1 minute of one another. Preferably, the administrations of the agents are spaced sufficiently close together that such a combinatorial effect is achieved. The agents can be administered simultaneously, for example, in a combined unit dose (providing simultaneous delivery of both agents). Alternatively, the agents can be administered at a specified time interval, for example, an interval or minutes, hours, days, or weeks. In general, however, the agents are concurrently bioavailable, e.g., detectable in the subject.

Exemplary anti-inflammatory agents include glucocorticoids and NSAIDS. Exemplary NSAIDS include salicylates, arylakanoic acids, 2-arylpropionic acids (profens), N-arylanthranilic acids (fenamic acids), pyrazolidine derivatives, oxicams, COX2 inhibitors, and sulphonanalides. Exemplary anti-inflammatory compounds include the following: Anti-inflammatory compounds include but are not limited to Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate;

Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium.

In some embodiments, a dendrimer described herein is combined with an analgesic. Analgesics are a class of drugs that includes most painkillers, such as aspirin, paracetamol (acetaminophen), and ibuprofen, e.g., and additional agents listed herein. Other examples include the nonsteroidal anti-inflammatory drugs (NSAIDs) such as salicylates, COX2 inhibitors, narcotic drugs such as morphine, and synthetic drugs with narcotic properties such as tramadol. Acetaminophen (Tylenol), Codeine (Tylenol #2, 3, 4), Darvocet (Propoxyphene/Acetaminophen), Darvon (Propoxyphene), Duragesic (Fentanyl Patch), Hydromorphone (Palladone, Dilaudid) Morphine (MSContin, Oramorph), Oxycodone (OxyContin, Roxicodone), Percocet (Oxycodone/Acetaminophen), Percodan (Oxycodone/Aspirin), Talwin NX (Pentazocine/Naloxone), Ultracet (Tramadol/Acetaminophen), Ultram (Tramadol), and Vicodin (Hydrocodone/Acetaminophen).

In some embodiments, a dendrimer described herein is combined with a salt of hyaluronic acid or a derivative thereof, for example, hylan, a cross-linked hyaluronic such as Synvisc or Hylastan, Seprafilm, or combinations thereof. (See, for example, U.S. Pat. Nos. 4,582,865; 4,713,448; 5,153,724; 5,099,013; 6,521,223, 5,017,229, 5,827,937, 7,226,972, and 6,921,819; and PCT publication WO 2005/066215 each of which is incorporated herein by reference.)

Dendrimer Containing Compositions

Pharmaceutical compositions of this invention comprise a dendrimer described herein or a pharmaceutically acceptable salt thereof; an additional compound including for example, an anti-inflammatory (e.g., a steroid) or an analgesic; and any pharmaceutically acceptable carrier, adjuvant or vehicle.

Compositions of this invention comprise a dendrimer described herein or a pharmaceutically acceptable salt thereof (e.g., where one or more terminal moieties of the dendrimer is a pharmaceutically acceptable salt); and a pharmaceutically acceptable carrier, adjuvant or vehicle. The compositions described herein include the dendrimers described herein, as well as additional therapeutic compounds if present, in amounts effective for achieving a modulation of disease or disease symptoms, including MMP mediated disorders or symptoms thereof. The compositions are made by methods including the steps of combining one or more dendrimers described herein with one or more carriers and, optionally, one or more additional therapeutic compounds described herein.

The term "pharmaceutically acceptable carrier or adjuvant" refers to a carrier or adjuvant that may be administered to a patient, together with a dendrimer described of this invention, and which does not destroy the pharmacological activity thereof and is nontoxic when administered in doses sufficient to deliver a therapeutic amount of the compound.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase which can be combined with emulsifying and/or suspending agents. If desired, certain sweetening and/or flavoring and/or coloring agents may be added.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. In some embodiments, a dendrimer described herein is combined with a salt of hyaluronic acid or a derivative thereof, for example, hylan, a cross-linked hyaluronic acid such as Synvisc or Hylastan, Seprafilm, or combinations thereof (See, for example, U.S. Pat. Nos. 4,582,865; 4,713,448; 5,153,724; 5,099,013; 6,521,223, 5,017,229, 5,827,937, 7,226,972, and 6,921,819; and PCT publication WO 2005/066215 each of which is incorporated herein by reference.) The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as D-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat. Cyclodextrins such as α-, β-, and γ-cyclodextrin, may also be advantageously used to enhance delivery of compounds of the formulae described herein.

In some cases, the pH of the formulation may be adjusted with pharmaceutically acceptable acids, bases or buffers to enhance the stability of the formulated compound or its delivery form.

The term parenteral as used herein includes subcutaneous, intracutaneous, intravenous, intramuscular, intraarticular, intraarterial, intrasynovial, intrasternal, intrathecal, intralesional, and intracranial injection or infusion techniques.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of this invention comprise a combination of a compound of the formulae described herein and one or more additional therapeutic or prophylactic agents, both the compound and the additional compound should be present at dosage levels of between about 1 to 100%, and more preferably between about 5 to 95% of the dosage normally administered in a monotherapy regimen. Additionally, combinations of a plurality of compounds described herein are also envisioned. The additional compounds may be administered separately, as part of a multiple dose regimen, from the compounds of this invention. Alternatively, those compounds may be part of a single dosage form, mixed together with the compounds of this invention in a single composition.

EXAMPLES

Examples 1 to 10 provide methods of making a dendrimer, for example, a dendrimer described herein. Exemplary dendrimers include modified PAMAM dendrimers such as generations 3.5, 2.5, and 1.5.

Example 1

Treatment of PAMAM Dendrimer Generation 3.5 with EDC with Dialysis Purification

A solution of 10% w/w PAMAM Dendrimer Generation 3.5 in methanol (6.0 g, 2.97 mmol COOH) was transferred into a 50 mL round bottom flask. Methanol was removed by rotary evaporation. A solution of 1-[3-(Dimethylamino)propyl]-3-ethylcarbodiimide hydrochloride (1.139 g, 5.94 mmol) in water (30 mL) was prepared. The EDC solution was added to the flask containing the dendrimer. The initial pH of the solution was measured at 8.83. The pH was adjusted with 1N HCl to 5.04. The reaction was clear and colorless. The reaction was allowed to go overnight with stirring at room temperature. At the completion of the reaction, the solution was loaded into dialysis tubing (SpectraPor 1000 MWCO) and dialyzed against PBS (two times) and against sterile water for injection (two times) over a period of several days to remove any EDU. The contents of the dialysis tubing were recovered by freeze drying. The product was a white, fine solid. Yield=0.4215 g.

Example 2

Treatment of PAMAM Dendrimer Generation 3.5 with EDC without Dialysis Purification A solution of 10% w/w PAMAM Dendrimer Generation 3.5 in methanol (5.0 mL, 2.48 mmol COOH) was transferred into a 50 mL conical tube. Methanol was allowed to evaporate overnight at room temperature. Water (8 mL) was added to the dried dendrimer. The conical tube was capped and placed on a rotator for 30 minutes. The resulting solution was homogeneous. The pH of the solution was between 9.5-10.0. The pH was adjusted by adding 2N HCl to pH of 4.5-5.0. A stock solution of 1-[3-(Dimethylamino)propyl]-3-ethylcarbodiimide hydrochloride (9.573 g, 49.9 mmol) in water (220 mL) was prepared. To the dendrimer solution was added 22.0 mL of the EDC stock solution corresponding to 4.96 mmol of EDC. The pH of the final reaction solution required additional adjustment to pH 4.5-5.0 with 2N HCl. The reaction was clear and colorless. The conical tube was capped and placed on a rotator overnight at room temperature. At the completion of the reaction, the solution was filtered using an Acrodisc Mustang E membrane at a rate of 1.0 mL per minute. The solution was aliquoted and stored at 2-8° C.

Example 3

Treatment of PAMAM Dendrimer Generation 3.5 with EDC in the Presence of Half Equivalent of Glucosamine A solution of 10% w/w PAMAM Dendrimer Generation 3.5 in methanol (6.0 g, 2.97 mmol COOH) was transferred into a 50 mL round bottom flask. Methanol was removed by rotary evaporation. A solution of Glucosamine hydrochloride (0.320 g, 1.48 mmol) in water (8 mL) was prepared and added to the flask. The pH of the reaction solution was adjusted to 5.0 with 1N HCl. A solution of 1-[3-(Dimethylamino)propyl]-3-ethylcarbodiimide hydrochloride (1.139 g, 5.94 mmol) in water (23 mL) was prepared. The EDC solution was added to the flask. The solution pH was measured and did not require adjustment. The reaction was clear and colorless. The reaction was allowed to go for 2 hours with stirring at room temperature. After 2 hours, 18 mL of the reaction solution was transferred into dialysis membrane (SpectraPor 1000 MWCO). The remaining reaction solution was allowed to go overnight with stirring at room temperature. At the completion of the reaction, the remaining solution was loaded into dialysis tubing (SpectraPor 1000 MWCO) and both samples were dialyzed against NaCl (two times) and against sterile water for injection (two times) over a period of several days to remove any EDU. The contents of the dialysis tubing were recovered by freeze drying. The product was a white, fine solid. Yield B1=0.2619 g; Yield B2=0.0112 g.

Example 4

Treatment of PAMAM Dendrimer Generation 3.5 with EDC in the Presence of Half Equivalent of Glucosamine A solution of 10% w/w PAMAM Dendrimer Generation 3.5 in methanol (6.0 g, 2.97 mmol COOH) was transferred into a 50 mL round bottom flask. Methanol was removed by rotary evaporation. A solution of Glucosamine hydrochloride (0.320 g, 1.48 mmol) in water (8 mL) was prepared and added to the flask. The pH of the reaction solution was adjusted to 5.0 with 1N HCl. A solution of 1-[3-(Dimethylamino)propyl]-3-ethylcarbodiimide hydrochloride (1.139 g, 5.94 mmol) in water (22 mL) was prepared. The EDC solution was added to the flask. The solution pH was measured and adjusted to 4.5-5.0 with 1N HCl. The reaction was clear and colorless. The reaction was allowed to go for 2 hours with stirring at room temperature. After 2 hours, 15 mL of the reaction solution was transferred into dialysis membrane (SpectraPor 1000 MWCO). The remaining reaction solution was allowed to go overnight with stirring at room temperature. At the completion of the reaction, the remaining 15 mL of solution was loaded into dialysis tubing (SpectraPor 1000 MWCO) and both samples were dialyzed against PBS (one time), NaCl (one time), and finally against sterile water for injection (one time) over a period of several days to remove any EDU. The contents of the dialysis tubing were recovered by freeze drying. The product was a white, fluffy solid. Yield C1=0.3007 g; Yield C2=0.3972 g.

Example 5

Treatment of PAMAM Dendrimer Generation 1.5 with EDC

A solution of 20% w/w PAMAM Dendrimer Generation 1.5 in methanol (~2.9 mL, 2.73 mmol COOH) was transferred into 4×50 mL conical tube. Methanol was allowed to evaporate overnight at room temperature. Water was added to the dried dendrimer. To reaction 78-1A was added 30 mL water, to 78-1B was added 25 mL, to 78-1C was added 20 mL, and to 78-1D was added 10 mL water. The conical tubes were capped and placed on a rotator for 30 minutes. The resulting solution was homogeneous. The pH of the solutions was between 9.5-10.0. The pH was adjusted by adding 2N HCl to pH of 4.5-5.0. A stock solution of 1-[3-(Dimethylamino)propyl]-3-ethylcarbodiimide hydrochloride (20.9 g, 0.109 mol) in water (100 mL) was prepared. To the reaction solution was added a volume of the EDC stock solution. To reaction 78-1A was added 0 mL of EDC solution, to 78-1B was added 5 mL EDC solution (5.45 mmol), to 78-1C was added 10 mL (10.9 mmol), and to 78-1D was added 20 mL (21.8 mmol). These volumes of the EDC solution correspond to 0 eq, 2 eq, 4 eq, and 8 eq of EDC. The pH of the final reaction solution required additional adjustment to pH 4.5-5.0 with 2N HCl. The reaction was clear and colorless. The conical tubes were capped and placed on a rotator overnight at room temperature. At the completion of the reaction, the solutions were filtered using an Acrodisc Mustang E membrane at a rate of 1.0 mL per minute. The solutions were aliquoted and stored at 2-8° C.

Example 6

Treatment of PAMAM Dendrimer Generation 2.5 with EDC

A solution of 10% w/w PAMAM Dendrimer Generation 1.5 in methanol (~6.3 mL, 2.554 mmol COOH) was transferred into 4×50 mL conical tube. Methanol was allowed to evaporate overnight at room temperature. Water was added to the dried dendrimer. To reaction 78-2A was added 30 mL water, to 78-2B was added 25 mL, to 78-2C was added 20 mL, and to 78-2D was added 10 mL water. The conical tubes were capped and placed on a rotator for 30 minutes. The resulting solution was homogeneous. The pH of the solutions was between 9.5-10.0. The pH was adjusted by adding 2N HCl to pH of 4.5-5.0. A stock solution of 1-[3-(Dimethylamino)propyl]-3-ethylcarbodiimide hydrochloride (20.9 g, 0.109 mol) in water (100 mL) was prepared. To the reaction solution was added a volume of the EDC stock solution. To reaction 78-1A was added 0 mL of EDC solution, to 78-1B was added 5 mL EDC solution (5.45 mmol), to 78-1C was added 10 mL (10.9 mmol), and to 78-1D was added 20 mL (21.8 mmol). These volumes of the EDC solution correspond to roughly 0 eq, 2 eq, 4 eq, and 8 eq of EDC. The pH of the final reaction solution required additional adjustment to pH 4.5-5.0 with 2N HCl. The reaction was clear and colorless. The conical tubes were capped and placed on a rotator overnight at room temperature. At the completion of the reaction, the solutions were filtered using an Acrodisc Mustang E membrane at a rate of 1.0 mL per minute. The solutions were aliquoted and stored at 2-8° C.

Example 7

Treatment of PAMAM Dendrimer Generation 3.5 with EDC Followed by Dialysis Purification. Synthesis of N-Acyl Urea Derivative of PAMAM Dendrimer Generation 3.5

A solution of 10% w/w PAMAM Dendrimer Generation 3.5 in methanol (9.0 g, 4.46 mmol COOH) was transferred into a 125 mL nalgene container. Methanol was allowed to evaporate overnight at room temperature. Sterile water for irrigation (15 mL) was added to the container. The solution was mixed at room temperature for 2 hours. The solution was clear, colorless, and homogeneous. The solution pH was measured and adjusted to 4.5-5.0 with 2N HCl. A solution of 1-[3-(Dimethylamino)propyl]-3-ethylcarbodiimide hydrochloride (2.277 g, 11.88 mmol) in water (60 mL) was prepared. The EDC solution (45 mL), corresponding to 8.91 mmol of EDC, was added to the flask containing the dendrimer. The pH was measured at 4.5-5.0 and did not require adjustment. The reaction was allowed to go overnight with stirring at room temperature. At the completion of the reaction, the solution was loaded into dialysis tubing (SpectraPor 3500 MWCO) and dialyzed against NaCl (two times) and against sterile water for injection (two times) over a period of several days to remove any EDU. The contents of the dialysis tubing were recovered by freeze drying. The product was a white solid. Yield=0.8184 g.

Example 8

Treatment of PAMAM Dendrimer Generation 3.5 with EDC in the Presence of AlexaFluor 488 Cadaverine A solution of 10% w/w PAMAM Dendrimer Generation 3.5 in methanol (1.0 g, 0.50 mmol COOH) was transferred into a 20 mL scintillation vial. Methanol was allowed to evaporate overnight at room temperature. Sterile water for irrigation (3.0 mL) was added to the vial. The solution was mixed at room temperature for 2 hours. The solution was clear, colorless, and homogeneous. The solution pH was measured and adjusted to 4.5-5.0 with 2N HCl. Water (1000 uL) was added to 2×1 mg of AF488. The AF488 solutions were dark green and were transferred into the reaction vial. The pH was measured at 4.68. A solution of 1-[3-(Dimethylamino)propyl]-3-ethylcarbodiimide hydrochloride (2.277 g, 11.88 mmol) in water (60 mL) was prepared. The EDC solution (5.0 mL), corresponding to 0.99 mmol of EDC, was added to the flask containing the dendrimer. The pH was measured at 4.5-5.0 and did not require adjustment. The reaction was allowed to go overnight at room temperature while protected from light. At the completion of the reaction, the solution was loaded into dialysis tubing (SpectraPor 3500 MWCO) and dialyzed against NaCl (two times) and against sterile water for injection (two times) over a period of several days to remove any EDU. The contents of the dialysis tubing were recovered by freeze drying. The product was a pink/orange solid. Yield=0.0881 g.

Example 9

Treatment of PAMAM Dendrimer Generation 3.5 with EDC and Half an Equivalent of Glucosamine without Dialysis Purification A solution of 10% w/w PAMAM Dendrimer Generation 3.5 in methanol (5.0 mL, 2.48 mmol COOH) was transferred into a 50 mL conical tube. Methanol was allowed to evaporate overnight at room temperature. A solution of Glucosamine hydrochloride (0.267 g, 1.24 mmol) in water (8 mL) was prepared and added to the flask. The conical tube was capped and placed on a rotator for 30 minutes. The resulting solution was homogeneous. The pH of the solution was between 7.5-8. The pH was adjusted by adding 2N HCl to pH of 4.5-5.0. A stock solution of 1-[3-(Dimethylamino)propyl]-3-ethylcarbodiimide hydrochloride (9.573 g, 49.9 mmol) in water (220 mL) was prepared. To the dendrimer solution was added 22.0 mL of the EDC stock solution corresponding to 4.96 mmol of EDC. The pH of the final reaction solution required additional adjustment to pH 4.5-5.0 with 2N HCl. The reaction was clear and colorless. The conical tube was capped and placed on a rotator overnight at room temperature. At the completion of the reaction, the solution was filtered using an Acrodisc Mustang E membrane at a rate of 1.0 mL per minute. The solution was aliquoted and stored at 2-8° C.

Example 10

Treatment of PAMAM Dendrimer Generation 3.5 with EDC

A solution of 10% w/w PAMAM Dendrimer Generation 3.5 in methanol (5.0 g, 2.48 mmol COOH) was transferred into 6×125 mL nalgene containers. Methanol was allowed to evaporate overnight at room temperature. Water was added to the dried dendrimer. To reactions 150-1 and 150-2 was added 30 mL water, to 150-3 was added 28 mL water, to 150-4 was added 25 mL, to 150-5 was added 20 mL, and to 150-6 was added 10 mL water. The containers were closed and mixed for 30 minutes. The resulting solution was homogeneous. The pH of the solutions was between 9.5-10.0. The pH was adjusted by adding 2N HCl to pH 4.5-5.0. A stock solution of 1-[3-(Dimethylamino)propyl]-3-ethylcarbodiimide hydrochloride (9.49 g, 4.95 mmol) in water (50 mL) was prepared. To the reaction solution was added a volume of the EDC stock solution. To reaction 150-1 was added 625 uL of EDC solution (0.62 mmol), to 150-2 was added 1250 uL EDC solution (1.24 mmol), to 150-3 was added 2500 uL EDC solution (2.48 mmol), to 150-4 was added 5 mL (4.96 mmol), to 150-5 was added 10 mL (9.92 mmol), and to 150-6 was added 20 mL (19.84 mmol). These volumes of the EDC solution correspond to roughly 0.25, 0.5 eq, 1.0 eq, 2 eq, 4 eq, and 8 eq of EDC. The pH of the final reaction solution was between pH 4.5-5.0 and did not require adjustment. The reaction was clear and colorless. The containers were closed and allowed to sit overnight at room temperature. At the completion of the reaction, the solutions were loaded into dialysis tubing (SpectraPor 3500 MWCO) and dialyzed against NaCl (two times) and against sterile water for injection (two times) over a period of several days to remove any EDU. The contents of the dialysis tubing were recovered by freeze drying. The product was a white solid. Yield=N/A.

Example 11

Evaluation of Terminal Modified PAMAM Generation 3.5 Dendrimers In Vitro

The effects of dendrimer compounds comprising n-acyl urea terminal moieties (i.e., dd-NAU) were evaluated for MMP activity in chondrocytes. The materials were prepared using methods described in Examples 2-9. In some instances, these effects were compared to dendrimer compounds comprising glucosamine terminal moieties (i.e., dd-Gln) and/or ethyl dimethylaminopropylurea (EDU). Chondrocytes were grown to confluency in 6-well plates (4 donors). The chondrocytes were pretreated with dendrimers (e.g., dd-NAU or dd-Gln) or EDU for 2 hours and then stimulated with IL-1β for 24 hours. Supernatants were collected and MMP-1, -3, and 13 ELISA assays were performed. The cells were collected for RNA analysis (3 donors).

The results of the assays are provided in FIGS. 1-10. FIGS. 1, 5, and 8 depict the effects of dd-NAU and dd-Gln on levels of active MMP-1, -3, and 13 respectively. These results are also compared to cells treated with EDU. FIGS. 2 and 6 depict the results of real-time PCR analysis of MMP-1 RNA and MMP-3 RNA respectively of cells treated with dd-NAU and dd-Gln. Real time PCT was also used to evaluate GAPDH RNA and MMP-3 RNA from cells treated with dd-NAU and dd-Gln the results of which are shown in FIG. 3 and FIG. 9 respectively. FIGS. 4, 7, and 10 depict the analysis of MMP-1, -3, and 13 respectively to normalized to GAPDH. $IC_{50}$ constants for inhibition of MMP activity is provided in Table 1 below:

TABLE 1

|  | Glucosamine (μM) | N-Acetyl glucosamine (μM) | Glucosamine Dendrimer (μM) | NAU Dendrimer (μM) | EDU (μM) |
|---|---|---|---|---|---|
| MMP-1 | 1420 | N/A | N/A | 16 | N/A |
| MMP-3 | 600 | N/A | N/A | 17 | N/A |
| MMP-13 | 1400 | N/A | N/A | 10 | N/A |

N/A = did not affect MMP levels $IC_{50}$ constants for inhibition of MMP mRNA levels are provided in Table 2 below:

TABLE 2

|  | NAU Dendrimer (μM) Protein | Glucosamine Dendrimer (μM) | NAU Dendrimer (μM) |
|---|---|---|---|
| MMP-1 | 16 | N/A | 15 |
| MMP-3 | 17 | N/A | 15 |
| MMP-13 | 10 | N/A | 10 |

N/A = did not affect MMP levels

Example 12

Evaluation of Terminal Modified PAMAM Generation 3.5 Dendrimers on Cartilage

The effects of dendrimer compounds comprising N-acyl urea terminal moieties (i.e., dd-NAU) prepared as described in Example 2 were evaluated on cartilage explants stimulated with IL-1β. Cartilage explants (6 mm punch) weighing 60-80 mg were prepared. The explants were stimulated with IL-1β in the presence of dd-NAU dd-Gln prepared as described in Example 9 or CMC for four days. Histological analysis was performed on the explants based on the procedures disclosed in Nishida et al., *Osteoarthritis Cartilage* 2004 May 12(5):374-82; and Soder et al., *Arthritis Rheum.* 2005 February 52(2):468-78.

FIG. 11 demonstrates the protective effects of dd-NAU on bovine cartilage relative to those treated with dd-Gln or CMC as provided by histological analysis.

FIGS. 12 and 13 demonstrate a chondroprotective role of dd-NAU as demonstrated in the normalized to wet weight of the cartilage (FIG. 12) and normalized to DNA (FIG. 13). These results show a dose response for chondroprotection with dd-NAU.

Example 13

Evaluation of Terminal Modified PAMAM Generation 3.5 Dendrimers In Vitro

Chondrocytes were grown to confluency in 6-well plates (2 donors). The chondrocytes were then pretreated with either a dendrimer as prepared in Example 2, a dd-Gln dendrimer prepared as described in Example 9, or an unmodified dendrimer. Supernatants were collected and MMP-1, -3, and 13 ELISA assays were performed. Neutral Red assays and Calcien AM assays were also performed on the chondrocytes to determine cell viability.

FIGS. 14-16 respectively demonstrate the effect of dd-NAU and dd-Gln on MMP-1, -3, and 13, production by human chondrocytes stimulated with IL-1β. FIG. 17 demonstrates the effect of the assayed compounds on cell viability. As seen by the data, cell viability remains high in cells treated with the assayed compounds.

Example 14

Evaluation of Terminal Modified PAMAM Generation 3.5 Dendrimers in Cartilage

Bovine cartilage explants (6 mm punch) weighing between 60 and 80 mgs were prepared. The explants were pretreated with one of dd-NAU prepared as described in, dd-Gln, EDU, or unmodified dendrimer for two hours. The dendrimers were prepared as described in Example 13. The cartilage was then stimulated with IL-1β (5 ng/ml) for four days. Histological and biochemical analysis were then performed on the samples.

FIG. 18 demonstrates the protective effect of the assayed compounds based on a histological analysis.

FIGS. 19 and 20 demonstrate the effect of dd-NAU, dd-Gln, EDU, or unmodified dendrimer on IL-1α induced proteoglycan loss in bovine cartilage explants.

Example 15

Evaluation of Terminal Modified PAMAM Generation 3.5 Dendrimers on LPS Induced Cytokine Production and Cell Viability in a THP-1 Macrophage Cell Line A THP-1 cell line (1E6) was plated in 24-wells. The cells were activated with PMA for 24 hours. The cells were then treated with one of dd-NAU, dd-Gln (made as described in Example 9), EDU, or unmodified dendrimer for two hours. The cells were then stimulated with LPS for 24 hours. Supernatants were then analyzed for cytokines.

FIGS. 21 and 22 demonstrate the effect of the assayed compounds on TNF-α and IL-1β production by human macrophages stimulated with LPS. dd-NAU inhibited LPS induced upregulation of pro-inflammatory cytokines (IL-1β, IL-6 and TNF-α) without adversely affecting cell viability as shown FIG. 23. FIG. 23 demonstrates the effect of the assayed compounds on cell viability. As seen by the data, cell viability remains high in cells treated with the assayed compounds.

Example 16

Evaluation of Terminal Modified Dendrimers In Vitro Using PAMAM Generation 1.5 and 2.5 Modified Dendrimers Modified dendrimers as prepared in Examples 5 and 6 were assayed using the protocols described in Example 13 for the effect of the compounds on MMP-1 production by human chondrocytes stimulated with IL-1β. These compounds were compared to those modified dendrimers as prepared according to Example FIG. 24 depicts the comparative effect of the modified PAMAM dendrimer of generation 1.5 with that of generation 2.5. As can be seen in the figures, both generations of dendrimers inhibited IL-1β induced MMP production. The levels of inhibition was similar to the level seen with the dendrimers prepared according to Example 2. The dendrimers also demonstrated an increase in potency by increasing the amount of EDA in the chemical reaction, for example, as provided in FIG. 25.

$IC_{50}$ values for the modified dendrimers are provided in Tables 3, 4, and 5 provided in the Appendix.

Example 17

Evaluation of Terminal Modified PAMAM Generation 1.5 and 2.5 Dendrimers on LPS Induced Cytokine Production and Cell Viability in a THP-1 Macrophage Cell Line THP-1 cells were prepared and assayed as described in Example 15. FIG. 26 demonstrates the effect of the modified generation 1.5 dendrimer on IL-1β production. Production was inhibited with treatment of the assayed compounds. The potency of the dendrimers was demonstrated to increase with dendrimers prepared using increasing amounts of EDC in the reaction mixtures.

A number of embodiments of the invention have been described. Nevertheless, it will be understood that various modifications may be made without departing from the spirit and scope of the invention. Accordingly, other embodiments are within the scope of the following claims.

What is claimed is:

1. A method of making a dendrimer,
   wherein the dendrimer comprises a plurality of branched repeating units radiating out from a central atom, multifunctional moiety, or cluster of atoms, wherein each repeating unit comprises a terminal moiety, wherein at least about 5% of the terminal moieties include a urea of formula (I)

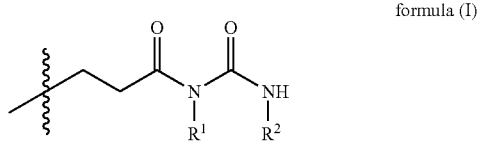

formula (I)

wherein
each of $R^1$ and $R^2$ is independently $C_1$-$C_6$ alkyl, $C_1$-$C_6$ alkenyl, cyclyl, aryl, heterocyclyl, heteroaryl, cyclylalkyl, arylalkyl, heterocyclylalkyl, or heteroarylalkyl; any of which are optionally substituted by $C_1$-$C_6$ alkyl, amino, $C_1$-$C_6$ alkylamino, $C_1$-$C_6$ dialkylamino, hydroxy, $C_1$-$C_6$ alkoxy, and wherein either of $R^1$ or $R^2$ independently optionally have a net charge;

∫ indicates the point of attachment of the terminal moiety of formula (I) to the dendrimer; and less than about 12% of the terminal moieties are covalently bound to a saccharide moiety, wherein the method comprises reacting a dendrimer comprising a plurality of terminal carboxylic acid moieties with a carbodiimide, wherein the carbodiimide is substituted with $R^1$ and $R^2$, thereby making the dendrimer.

2. The method of claim 1, wherein less than about 10% of the terminal moieties are covalently bound to a saccharide moiety.

3. The method of claim 1, wherein either of $R^1$ or $R^2$ has a net positive charge.

4. The method of claim 1, wherein $R^1$ and $R^2$ are both cyclohexyl.

5. The method of claim 1, wherein $R^1$ and $R^2$ are both isopropyl.

6. The method of claim 1, wherein one of $R^1$ and $R^2$ is ethyl and the other of $R^1$ and $R^2$ is dimethylaminopropyl.

7. The method of claim 1, wherein one of $R^1$ and $R^2$ is cyclohexyl and the other of $R^1$ and $R^2$ is morpholinoethyl.

8. The method of claim 1, wherein each of $R^1$ and $R^2$ is independently $C_1$-$C_6$ alkyl, and one of $R^1$ and $R^2$ is substituted by $C_1$-$C_6$ dialkylamino and has a positive net charge.

9. The method of claim 1, wherein a terminal moiety includes a urea of formula (I')

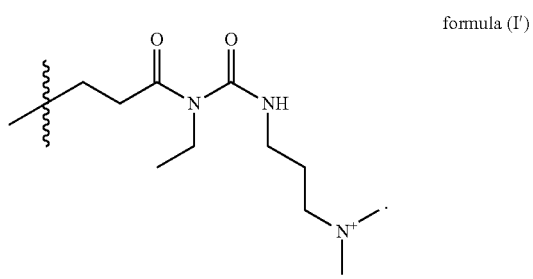 [SMILES: *CCC(=O)N(CC)C(=O)NCCC[NH+](C)C]

formula (I')

10. The method of claim 1, wherein a terminal moiety includes a urea of formula (I")

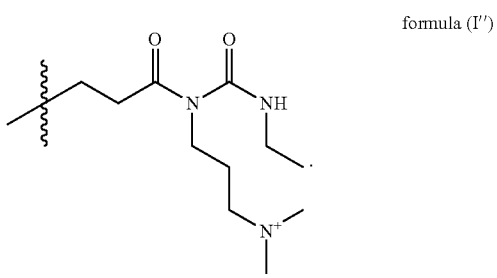 [SMILES: *CCC(=O)N(CCC[NH+](C)C)C(=O)NCC]

formula (I")

11. The method of claim 1, wherein at least about 5% of the terminal moieties include a urea of formula (I'), formula (I"), or a combination thereof.

12. The method of claim 1, wherein the dendrimer is selected from the group consisting of a polyamidoamine dendrimer, a polypropylene dendrimer, a polyethyleneimine dendrimer, a carbohydrate based dendrimer, a peptide based dendrimer, a glycopeptide dendrimer, a metal containing dendrimer, a poly aryl amine dendrimer, a polyamide dendrimer, a poly (alkyl amine) dendrimer, a polyamido alcohol dendrimer, a cyano dendrimer, a polyether dendrimer, a polythioether dendrimer, a polysiloxane dendrimer, a dendritic aryl ester, a perchlorinated dendrimer, a catalytic center containing dendrimer, a silicon containing dendrimer, a phosphorus containing dendrimer, and a hydrocarbon dendrimer.

13. The method of claim 12, wherein the dendrimer is a polyamidoamine dendrimer.

14. The method of claim 1, wherein at least about 80% of the terminal moieties are terminated with a carboxylate.

15. The method of claim 14, wherein the dendrimer is a polyamidoamine dendrimer.

16. The method of claim 1, wherein the dendrimer is a polyamidoamine dendrimer, and wherein at least about 50% of the terminal moieties are terminated with a carboxylate group.

17. The method of claim 1, wherein the dendrimer is a polyamidoamine dendrimer of generation 0.5, 1.5, 2.5, 3.5, 4.5, 5.5, 6.5, 7.5, 8.5, or 9.5.

18. The method of claim 1, wherein the dendrimer is a polyamidoamine dendrimer of generation 0.5, 1.5, 2.5, or 3.5 with a carboxylate terminal moiety.

19. The method of claim 1, wherein the dendrimer of formula (I) is made by reacting one or more terminal moieties of a starting dendrimer with a carbodiimide of formula (II) $R^1-N=C=N-R^2$.

* * * * *